United States Patent
Gassman

(10) Patent No.: US 10,589,014 B2
(45) Date of Patent: Mar. 17, 2020

(54) MEDICAL FLUID DELIVERY SYSTEM INCLUDING REMOTE MACHINE UPDATING AND CONTROL

(71) Applicants: Baxter International Inc., Deerfield, IL (US); Baxter Healthcare SA, Glattpark (Opfikon) (CH)

(72) Inventor: Christopher Daniel Gassman, Crystal Lake, IL (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 0 days.

(21) Appl. No.: 15/386,913

(22) Filed: Dec. 21, 2016

(65) Prior Publication Data
US 2018/0169314 A1    Jun. 21, 2018

(51) Int. Cl.
| A61M 1/16 | (2006.01) |
| A61M 1/28 | (2006.01) |
| A61M 5/14 | (2006.01) |
| G08B 5/22 | (2006.01) |

(52) U.S. Cl.
CPC .......... *A61M 1/1601* (2014.02); *A61M 1/28* (2013.01); *A61M 5/14* (2013.01); *G08B 5/223* (2013.01); *A61M 2205/18* (2013.01); *A61M 2205/3553* (2013.01); *A61M 2205/70* (2013.01)

(58) Field of Classification Search
CPC ................ A61M 1/1601; A61M 1/28; A61M 2205/3561; A61M 5/14; G08B 5/223
See application file for complete search history.

(56) References Cited

U.S. PATENT DOCUMENTS

| 4,464,172 A | 8/1984 | Lichtenstein |
| 5,151,082 A | 9/1992 | Gorsuch et al. |
| 5,247,434 A | 9/1993 | Peterson et al. |
| 5,486,286 A | 1/1996 | Peterson et al. |

(Continued)

FOREIGN PATENT DOCUMENTS

| CN | 1950125 | 4/2007 |
| CN | 1960775 | 5/2007 |

(Continued)

OTHER PUBLICATIONS

Manns et al., The acu-menTM: A new device for continuous renal replacement therapy in actue renal failure, Kidney International, 1998, pp. 268-274, vol. 54.

(Continued)

*Primary Examiner* — Kabir A Timory
(74) *Attorney, Agent, or Firm* — K&L Gates LLP

(57) ABSTRACT

A medical fluid delivery system in one embodiment includes: a first medical fluid delivery machine configured to generate a first message for remote transmission to a first patient or caregiver indicating (i) that the first medical fluid delivery machine is ready to perform a task or (ii) a preprogrammed time for the first medical fluid delivery machine to perform a task; and a second medical fluid delivery machine configured to generate a second message for remote transmission to a second patient or caregiver indicating (i) that the second medical fluid delivery machine is ready to perform a task or (ii) a preprogrammed time for the second medical fluid delivery machine to perform a task.

29 Claims, 9 Drawing Sheets

(56) References Cited

U.S. PATENT DOCUMENTS

| | | |
|---|---|---|
| 5,732,401 A | 3/1998 | Conway |
| 5,764,923 A | 6/1998 | Tallman et al. |
| 5,788,851 A | 8/1998 | Kenley et al. |
| 5,867,821 A | 2/1999 | Ballantyne et al. |
| 5,919,154 A | 7/1999 | Toavs et al. |
| 5,933,136 A | 8/1999 | Brown |
| 6,230,142 B1 | 5/2001 | Benigno et al. |
| 6,471,382 B2 | 10/2002 | Eichhorn |
| 6,685,831 B2 | 2/2004 | Donig |
| 7,044,927 B2 | 5/2006 | Mueller et al. |
| 7,072,769 B2 | 7/2006 | Fletcher-Haynes et al. |
| 7,185,282 B1 | 2/2007 | Naidoo et al. |
| 7,801,598 B2 | 9/2010 | Zhu et al. |
| 7,801,746 B2 | 9/2010 | Moll et al. |
| 7,890,341 B2 | 2/2011 | McNally et al. |
| 8,062,513 B2 | 11/2011 | Yu et al. |
| 8,095,390 B2 | 1/2012 | Bluemler et al. |
| 8,178,040 B2 | 5/2012 | Brauer |
| 8,257,582 B2 | 9/2012 | Yu et al. |
| 8,267,308 B2 | 9/2012 | Devergne et al. |
| 8,315,654 B2 | 11/2012 | Balschat et al. |
| 8,321,044 B2 | 11/2012 | Plahey et al. |
| 8,543,420 B2 | 9/2013 | Darby et al. |
| 8,632,485 B2 | 1/2014 | Schlaeper et al. |
| 8,679,075 B2 | 3/2014 | Lurvey |
| 8,698,741 B1 | 4/2014 | Wang et al. |
| 8,769,625 B2 | 7/2014 | Wang |
| 8,823,500 B2 | 9/2014 | Heath |
| 8,836,519 B2 | 9/2014 | Wright et al. |
| 8,906,240 B2 | 12/2014 | Crnkovich et al. |
| 8,926,550 B2 | 1/2015 | Plahey et al. |
| 9,081,382 B2 | 7/2015 | Doyle et al. |
| 9,178,891 B2 | 11/2015 | Wang et al. |
| 9,250,216 B2 | 2/2016 | Wright et al. |
| 9,333,286 B2 | 5/2016 | Wright et al. |
| 9,408,958 B2 | 8/2016 | Wang et al. |
| 9,517,295 B2 | 12/2016 | Wilt et al. |
| 2002/0040282 A1 | 4/2002 | Bailey |
| 2002/0082728 A1 | 6/2002 | Mueller |
| 2002/0087361 A1 | 7/2002 | Benigno et al. |
| 2002/0103453 A1 | 8/2002 | Burbank et al. |
| 2002/0147423 A1 | 10/2002 | Burbank et al. |
| 2003/0220598 A1 | 11/2003 | Busby |
| 2004/0111294 A1 | 6/2004 | McNally |
| 2004/0115132 A1 | 6/2004 | Young et al. |
| 2004/0172222 A1 | 9/2004 | Simpson et al. |
| 2005/0021370 A1 | 1/2005 | Riff et al. |
| 2005/0055242 A1 | 3/2005 | Bello et al. |
| 2005/0277890 A1 | 12/2005 | Stewart et al. |
| 2005/0277911 A1 | 12/2005 | Stewart et al. |
| 2007/0112603 A1 | 5/2007 | Kauthen et al. |
| 2008/0040151 A1 | 2/2008 | Moore |
| 2008/0154177 A1 | 6/2008 | Moubayed et al. |
| 2008/0215627 A1 | 9/2008 | Higgins et al. |
| 2008/0268413 A1 | 10/2008 | Leichner |
| 2009/0164248 A1 | 6/2009 | Hunt |
| 2010/0010428 A1 | 1/2010 | Yu et al. |
| 2010/0137693 A1 | 6/2010 | Porras |
| 2011/0004351 A1 | 1/2011 | Kelly et al. |
| 2011/0087501 A1 | 4/2011 | Severin |
| 2011/0172744 A1 | 7/2011 | Davis et al. |
| 2011/0257891 A1 | 10/2011 | Akonur |
| 2012/0029937 A1 | 2/2012 | Neftel |
| 2012/0081225 A1 | 4/2012 | Waugh |
| 2012/0138533 A1 | 6/2012 | Curtis |
| 2012/0182939 A1 | 7/2012 | Rajan et al. |
| 2012/0212455 A1 | 8/2012 | Kloeffel |
| 2012/0238851 A1 | 9/2012 | Kamen |
| 2012/0289928 A1 | 11/2012 | Wright et al. |
| 2013/0018355 A1 | 1/2013 | Brand et al. |
| 2013/0020237 A1 | 1/2013 | Wilt et al. |
| 2013/0037485 A1 | 2/2013 | Wilt et al. |
| 2013/0133036 A1 | 5/2013 | Wang |
| 2013/0191513 A1 | 7/2013 | Kamen et al. |
| 2013/0310735 A1 | 7/2013 | Yu et al. |
| 2013/0211206 A1 | 8/2013 | Sands et al. |
| 2013/0297330 A1 | 11/2013 | Kamen et al. |
| 2013/0317753 A1 | 11/2013 | Kamen et al. |
| 2013/0317837 A1 | 11/2013 | Ballantyne et al. |
| 2014/0012595 A1 | 1/2014 | Fox et al. |
| 2014/0039447 A1 | 2/2014 | Wright et al. |
| 2014/0091022 A1 | 4/2014 | Raiford et al. |
| 2014/0188516 A1 | 7/2014 | Kamen et al. |
| 2014/0222450 A1* | 8/2014 | Gray .................. G06F 19/3468 705/2 |
| 2014/0266983 A1 | 9/2014 | Christensen |
| 2014/0267003 A1 | 9/2014 | Wang et al. |
| 2014/0289812 A1 | 9/2014 | Wang et al. |
| 2014/0298171 A1 | 10/2014 | Wang et al. |
| 2014/0299544 A1 | 10/2014 | Wilt et al. |
| 2014/0345386 A1 | 11/2014 | Wright et al. |
| 2015/0018758 A1* | 1/2015 | John ...................... G06F 19/00 604/67 |
| 2015/0112264 A1 | 4/2015 | Kamen |
| 2015/0154364 A1 | 6/2015 | Biasi et al. |
| 2015/0196699 A9 | 7/2015 | Wilt et al. |
| 2015/0253860 A1 | 9/2015 | Merics et al. |
| 2016/0021191 A1 | 1/2016 | Wang et al. |
| 2016/0030655 A1 | 2/2016 | Wright et al. |
| 2016/0055303 A1 | 2/2016 | Keller |
| 2016/0058933 A1 | 3/2016 | Ballantyne et al. |
| 2016/0206800 A1 | 7/2016 | Tanenbaum et al. |
| 2016/0239637 A1 | 8/2016 | Miller |
| 2016/0261974 A1 | 9/2016 | Arrizza |
| 2016/0310653 A1 | 10/2016 | Wang et al. |
| 2016/0356874 A1 | 12/2016 | Wang et al. |
| 2017/0000938 A1 | 1/2017 | Wilt et al. |
| 2017/0011175 A1 | 1/2017 | Cocks et al. |

FOREIGN PATENT DOCUMENTS

| | | |
|---|---|---|
| CN | 101606157 | 12/2009 |
| CN | 101611409 | 12/2009 |
| EP | 0611228 | 8/1994 |
| EP | 1195708 | 4/2002 |
| EP | 1 235 614 | 9/2002 |
| EP | 2368588 | 9/2011 |
| WO | 9014850 | 12/1990 |
| WO | 94/24929 | 11/1994 |
| WO | 99/46657 | 7/1999 |
| WO | 99/52025 | 10/1999 |
| WO | 2001/37786 | 5/2001 |
| WO | 2002/078783 | 10/2002 |
| WO | 2004/069095 | 8/2004 |
| WO | 2004/070546 | 8/2004 |
| WO | 2004/070548 | 8/2004 |
| WO | 2004/070549 | 8/2004 |
| WO | 2004/070556 | 8/2004 |
| WO | 2004/070557 | 8/2004 |
| WO | 2004/070562 | 8/2004 |
| WO | 2004/070994 | 8/2004 |
| WO | 2004/070995 | 8/2004 |
| WO | 2005/101279 | 10/2005 |
| WO | 2010056712 | 5/2010 |
| WO | 2014052596 | 4/2014 |
| WO | 2014100687 | 6/2014 |
| WO | 2014144909 | 9/2014 |
| WO | 2015183981 | 12/2015 |
| WO | 2016144541 | 9/2016 |
| WO | 2016196325 | 12/2016 |
| WO | 2017011197 | 1/2017 |

OTHER PUBLICATIONS

Supplementary International Search Report for Application No. PCT/US2013/040967 dated Jun. 19, 2014.

Letter from Mexican associate regarding office action for MX/a/2007/014394 dated Mar. 12, 2013.

European office action for Application No. 11 075 130.2-1651 dated Sep. 23, 2013.

European office action for Application No. 11 075 130.2-1651 dated Oct. 6 2014.

(56) References Cited

OTHER PUBLICATIONS

Patent Examination Report No. 1—Australia, dated Aug. 18, 2015, Patent Application No. 2013263015—7 pages.
Wang, Samuel J. et al. User-Definable Medication Favorites for an Outpatient Electronic Medical Record System. Proc AMIA Symp. 2001 : 1055.
Opposition against EP 2368588 (EP Application 11075130.2) mailed May 13, 2016, 30 pages.
Office Action issued in U.S. Appl. No. 15/088,966, dated Jun. 20, 2016, 17 pages.
Office Action issued in U.S. Appl. No. 15/135,837, dated Aug. 12, 2016, 17 pages.
Office Action issued in U.S. Appl. No. 13/828,900, dated Aug. 8, 2016, 28 pages.
Office Action issued in U.S. Appl. No. 13/828,900, dated Jan. 25, 2016, 28 pages.
Office Action issued in CN Application 201380031530.6 dated Aug. 1, 2016, 12 pages.
Office Action issued in AU Application 2013263015 dated Aug. 16, 2016, 6 pages.
Office Action issued in U.S. Appl. No. 15/135,810, dated Jun. 28, 2016, 18 pages.
4008H Hemodialysis Machine Operation Instructions, Software Version 4.2, Fresenius Medical Care.
Tsavdaris, et al., "Monitoring and Supporting Home Maemodialysis using Telematic Services", Decision Support Systems Laboratory, National Technical University of Athens, Wire Communications Laboratory, University of Patras.
B. Agroyannis, et al. "Telemedicine technology and applications for home hemodialysis", The International Journal of Artificial Organs, vol. 22/No. 10, 1999/ pp. 679-683.
Contents, The International Journal of Artificial Organs, vol. 22/No. 10—1999/pp. 657-722.
Proceedings of the 19th Annual International Conference of the IEEE Engineering in Medicine and Biology Society, Oct. 30-Nov. 2, 1997, Chicago, IL USA.
Notice of opposition to a European patent, Patent No. EP 1 235 614, dated May 8, 2013.
Opposition Statement, Patent No. EP 1 235 614 B, dated May 8, 2013.
Notice of opposition to a European patent, Patent No. EP2366588, dated Jun. 14, 2016.
Reexamination Certificate, U.S. Pat. No. B1 5,211,349, Certificate issued May 27, 1997.
Decision on Opposition, European Patent No. 1 235 614 dated Jul. 30, 2015.
Non-Final Office Action dated Jun. 20, 2016 in U.S. Appl. No. 15/088,966.
Final Office Action dated Nov. 25, 2016 in U.S. Appl. No. 15/088,966.
Non-Final Office Action dated Jun. 28, 2016 in U.S. Appl. No. 15/135,810.
Final Office Action dated Jan. 4, 2017 in U.S. Appl. No. 15/135,810.
Non-Final Office Action dated Aug. 12, 2016 in U.S. Appl. No. 15/135,837.
Final Office Action dated Feb. 3, 2017 in U.S. Appl. No. 15/135,837.
Mexican Office Action dated Dec. 14, 2016 in corresponding Mexican Application No. MX/a/2014/013920.
Chinese Office Action dated Feb. 21, 2017 in corresponding Chinese Application No. 201380031530.6.
New Zealand Office Action dated Mar. 10, 2017 in corresponding New Zealand Application No. 702249.
Canadian Office Action dated Feb. 24, 2017 in corresponding Canadian Application No. 2,873,621—4 pages.
International Search Report—PCT/US2017/067662 dated Jun. 13, 2018—9 pages.
Written Opinion of the International Searching Authority date of mailing—PCT/US2017/067662—18 pages.

\* cited by examiner

MEDICAL FLUID DELIVERY SYSTEM INCLUDING REMOTE MACHINE UPDATING AND CONTROL

BACKGROUND

The present disclosure relates generally to devices, systems and methods for medical fluid delivery machines. More specifically, the present disclosure relates to the interaction between medical fluid delivery machines and a patient or caregiver's mobile communication device.

One relevant medical fluid delivery machine is a renal failure therapy machine. Regarding renal failure therapy machines, due to various causes, a person's renal system can fail. Renal failure produces several physiological derangements. It is no longer possible to balance water and minerals or to excrete daily metabolic load. Toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that frequent treatments remove more toxins and waste products than a patient receiving less frequent but perhaps longer treatments. A patient receiving treatments more frequently does not experience as much of a down cycle as does an in-center patient, who has built-up two or three days' worth of toxins prior to treatment. In certain areas, the closest dialysis center can be many miles from the patient's home causing door-to-door treatment time to consume a large portion of the day. HHD may take place overnight or during the day while the patient relaxes, works or is otherwise productive.

Another type of kidney failure therapy is peritoneal dialysis, which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane and into the dialysis fluid due to diffusion and osmosis, i.e., an osmotic gradient occurs across the membrane. An osmotic agent in dialysis provides the osmotic gradient. The used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), and tidal flow dialysis and continuous flow peritoneal dialysis ("CFPD"). CAPD is a manual dialysis treatment. Here, the patient manually connects an implanted catheter to a drain to allow used or spent dialysate fluid to drain from the peritoneal cavity. The patient then connects the catheter to a bag of fresh dialysis fluid to infuse fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to perform the treatment cycles manually and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid bags.

APD machines pump used or spent dialysate from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

Any of the above modalities performed by a machine may be run on a scheduled basis and may require a start-up procedure. For example, dialysis patients typically perform treatment on a scheduled basis, such as every other day, daily, etc. Blood treatment machines typically require a certain amount of time before treatment for setup, for example, to run a disinfection procedure. Patients for the above modalities may lead busy lives and have projects to perform or errands to run on a day scheduled for treatment. One solution purporting to be helpful to patients is disclosed in U.S. Pat. No. 8,315,654 ("the '654 Patent"), entitled, "Extracorporeal Blood Treatment Device And Method For Preparing Blood Treatment Using An Extracorporeal Blood Treatment Device". The '654 Patent discloses a regime in which the patient sends an initiation code from an external communication unit to a blood treatment device to initiate routines at the blood treatment device. (See the '654 Patent at Abstract). As discussed in more detail below, however, the regime of the '654 Patent does not take into account certain important factors related to the machine and to the treatment itself.

An improved regime for enabling a patient to interact remotely with a medical fluid delivery machine is needed accordingly.

SUMMARY

The medical fluid data transfer system and methodology of the present disclosure is applicable, for example, to fluid delivery for: plasmapherisis, hemodialysis ("HD"), hemofiltration ("HF") hemodiafiltration ("HDF"), and continuous renal replacement therapy ("CRRT") treatments. The medical fluid data transfer system described herein is also applicable to peritoneal dialysis ("PD"), intravenous drug delivery, and nutritional fluid delivery. These modalities may be referred to herein collectively or generally individually as medical fluid delivery.

The above modalities may be provided by a medical fluid delivery machine that houses components needed to deliver medical fluid, such as one or more pump, plural valves, a heater if needed, online medical fluid generation equipment if needed, plural sensors, such as any one, or more, or all of pressure sensors, conductivity sensors, temperature sensors, air detectors, blood leak detectors, and the like, a user interface, and a control unit, which may employ one or more processor and memory to control the above-described equipment. The medical fluid delivery machine may also include one or more filter, such as a dialyzer or hemofilter for cleansing blood and/or an ultrafilter for purifying water, dialysis fluid, or other fluid.

The medical fluid delivery machine and the medical fluid data transfer system and methodology described herein may be used with home-based machines. For example, the systems may be used with home HD, HF or HDF machines, which are operated at the patient's convenience. One such home system is described in U.S. Pat. No. 8,029,454 ("the '454 Patent"), issued Oct. 4, 2011, entitled "High Convection Home Hemodialysis/Hemofiltration And Sorbent System", filed Nov. 4, 2004, assigned to the assignee of the present application. Other such home systems are described in U.S. Pat. No. 8,393,690 ("the '690 Patent"), issued Mar. 12, 2013, entitled "Enclosure for a Portable Hemodialysis System", filed Aug. 27, 2008. The entire contents of each of the above references are incorporated herein by reference and relied upon.

Much of the appeal of a home treatment for the patient revolves around the lifestyle flexibility provided by allowing the patient to perform treatment in his or her home largely according to his or her own schedule. The home medical fluid delivery machine may however include software timers that dictate to and constrain the user or patient. A home hemodialysis system may for example require the patient to be in immediate proximity to the home hemodialysis machine to initiate pre-treatment, during treatment, and post-treatment sequences.

In one particular example, a home therapy machine may reuse certain components by disinfecting them in between treatments. The machine may employ one or more disinfection timer that requires the patient or caregiver to start a treatment using the machine before the disinfection timer expires. Otherwise, the patient will have to wait until another disinfection procedure is completed before starting treatment. The home therapy machine in an embodiment communicates the treatment start time deadlines via the machine's graphical user interface, which requires the patient to be in the proximity of the machine to access the start time deadlines and react accordingly.

It should be appreciated that the present disclosure applies to any type of disinfection, such as, hot water disinfection and chemical disinfection. In this regard, the present disclosure is not limited to home therapy machines, for example, in-center machines are typically chemically disinfected and may set a treatment start deadline after such disinfection. Further additionally, the present disclosure is not limited to start time deadlines based upon disinfection but may also be applied to other start time deadlines, e.g., ones based upon the completion of priming. Still further, the present disclosure is not limited to initial start time deadlines. For example, most machines will allow the patient to temporarily stop treatment and disconnect from the machine to perform some type of necessary action away from the machine. For a blood treatment, the machine will typically rinse blood back to the patient and may or may not circulate the dialysis fluid for a period of time. In either case, the time that the patient may be temporarily disconnected from the machine is not unlimited, and it is contemplated that the present disclosure also applies to the return time limit.

In one embodiment, the system of the present disclosure provides a software application ("app") that is installed on the patient's and/or caregiver's personal mobile communication device, e.g., smartphone. The app is provided in one embodiment via a middleware software application, an example of which is discussed in detail below. In an alternative embodiment, the software is configured to communicate with the patient's and/or caregiver's personal mobile communication device, e.g., smartphone, directly using a text messaging feature through a middleware software application. In either case, the app or text message is structured in one embodiment to remind the patient of any impending deadline and to allow the patient and/or caregiver to keep track of when a treatment needs to start without tethering the patient to the machine.

It is contemplated to alternatively or additionally structure the communication software to program reminders automatically on the user's mobile communication device, for example, on the device's native task tracking features, such as a calendar application. Most smartphones are provided with a calendar that separates each day into time segments, such as hours. The software of the system and methodology of the present disclosure may be programmed to access the smartphone calendars of authorized patients and/or caregivers and to populate the appropriate time segment(s) of the appropriate day with the appropriate information, for example, that the machine is to begin or complete disinfection within that time segment.

In one embodiment, communication from the software system and methodology of the present disclosure is one-way. For example, communication may be from the medical fluid delivery machine, which may be a home machine, to a patient or caregiver's mobile communication device. In an alternative embodiment, the software system and methodology of the present disclosure enables two-directional communication between the medical fluid delivery machine and the patient or caregiver's mobile communication device. In one example, the two-way communication may allow for certain machine routines to be started remotely by the patient or caregiver using their mobile communication device. One example routine is an automated self-test routine, which may be performed without any user interaction with the system other than initiating or starting the sequence. Starting the sequence remotely may benefit the patient or caregiver, e.g., by providing additional time that the patient or caregiver may be away from the machine performing other tasks. The communication becomes two-way when the machine initiates the communication by indicating that the machine is ready to perform the self-test routine. The patient or caregiver at a desired time responds back to the machine via the software system and methodology of the present disclosure to initiate the sequence.

It is contemplated for the software of the system and methodology of the present disclosure to disable communication between the patient and/or caregiver and the machine whenever the machine is in a "patient connected" software state. For example, if a clinician tries to send a command to a machine currently treating a patient, the command may be intercepted by the middleware software application so that the command is not transferred to the machine. The middleware software application may then communicate back to the clinician informing that the machine is busy and not accepting communication.

As described in detail below, the medical fluid data transfer system and methodology of the present disclosure may operate within a larger platform system encompassing many machines including many different types of machines, patients, clinicians, doctors, service personnel, electronic medical records ("EMR") databases, a website, a resource planning system handling data generated via the patient and clinician communications, and business intelligence. The medical fluid data transfer system and methodology of the present disclosure operates seamlessly within the overall system and without contravening its rules and protocols.

Also disclosed herein is a system specifically configured for a hospital or clinical setting, which allows a single doctor, nurse or clinician to monitor and possibly control multiple medical fluid delivery machines. The hospital or clinical system allows multiple machines to be viewed, and possibly controlled via a single mobile communication device.

In light of the disclosure herein and without limiting the disclosure in any way, in a first aspect of the present disclosure, which may be combined with any other aspect listed herein unless specified otherwise, a medical fluid delivery system includes: a first medical fluid delivery machine configured to generate a first message for remote transmission to a first patient or caregiver indicating (i) that the first medical fluid delivery machine is ready to perform a task or (ii) a preprogrammed time for the first medical fluid delivery machine to perform the same or a different task; and a second medical fluid delivery machine configured to generate a second message for remote transmission to a second patient or caregiver indicating (i) that the second medical fluid delivery machine is ready to perform the same or a different task or (ii) a preprogrammed time for the second medical fluid delivery machine to perform the same or a different task.

In a second aspect of the present disclosure, which may be combined with any other aspect listed herein unless specified otherwise, the first and second medical fluid delivery machines are in data communication with at least one server, the first and second messages delivered to the server, the server configured to (i) relay the first message to a first mobile communication device for the first patient or caregiver and (ii) relay the second message to a second mobile communication device for the second patient or caregiver.

In a third aspect of the present disclosure, which may be combined with the second aspect in combination with any other aspect listed herein unless specified otherwise, the at least one server includes at least one dedicated server or a cloud server.

In a fourth aspect of the present disclosure, which may be combined with the second aspect in combination with any other aspect listed herein unless specified otherwise, relaying at least one of the first or second messages includes using a cellular network networking the at least one server and at least one of the first or second mobile communication devices.

In a fifth aspect of the present disclosure, which may be combined with the fourth aspect in combination with any other aspect listed herein unless specified otherwise, communication over the cellular network is via a Short Messaging Service ("SMS") or Multimedia Messaging Service ("MMS") protocol.

In a sixth aspect of the present disclosure, which may be combined with the second aspect in combination with any other aspect listed herein unless specified otherwise, the first and second medical fluid delivery machines are home machines in data communication with the at least one server via an internet connection.

In a seventh aspect of the present disclosure, which may be combined with the second aspect in combination with any other aspect listed herein unless specified otherwise, the first and second medical fluid delivery machines are in-center machines, wherein the at least one server is maintained at the center.

In an eighth aspect of the present disclosure, which may be combined with the second aspect in combination with any other aspect listed herein unless specified otherwise, relaying by the at least one server of at least one of the first or second messages includes updating a software application downloaded onto at least one of the first or second mobile communication devices.

In a ninth aspect of the present disclosure, which may be combined with the eighth aspect in combination with any other aspect listed herein unless specified otherwise, the at least one software application is downloaded from the system.

In a tenth aspect of the present disclosure, which may be combined with the second aspect in combination with any other aspect listed herein unless specified otherwise, relaying by the at least one server of at least one of the first or second messages includes updating a calendar installed on at least one of the first or second mobile communication devices.

In an eleventh aspect of the present disclosure, which may be combined with any other aspect listed herein unless specified otherwise, the same or a different task includes a start-up procedure task.

In a twelfth aspect of the present disclosure, which may be combined with any other aspect listed herein unless specified otherwise, the same or a different task includes a disinfection procedure or a self-test routine.

In a thirteenth aspect of the present disclosure, which may be combined with any other aspect listed herein unless specified otherwise, the preprogrammed time for at least one of the first or second medical fluid delivery machines is (i) a set duration from when the first or second message is generated or (ii) a time programmed for the same or a different task to begin.

In a fourteenth aspect of the present disclosure, which may be combined with any other aspect listed herein unless specified otherwise, a medical fluid delivery system includes: a medical fluid delivery machine configured to generate a message indicating (i) that the medical fluid delivery machine is ready to perform a task or (ii) a preprogrammed time for the medical fluid delivery machine to perform the same or a different task; and at least one server in data communication with the medical fluid delivery machine to receive the message, the at least one server including middleware software for relaying the message from the medical fluid delivery machine to a remote mobile communication device.

In a fifteenth aspect of the present disclosure, which may be combined with the fourteenth aspect in combination with any other aspect listed herein unless specified otherwise, the middleware software updates a software application downloaded onto the mobile communication device to relay the message.

In a sixteenth aspect of the present disclosure, which may be combined with the fourteenth aspect in combination with any other aspect listed herein unless specified otherwise, the middleware software updates a calendar installed on the mobile communication device to relay the message.

In a seventeenth aspect of the present disclosure, which may be combined with the fourteenth aspect in combination with any other aspect listed herein unless specified otherwise, the middleware software uses a cellular communications network networking the at least one server and at least one of the first or second mobile communication devices to relay the message.

In an eighteenth aspect of the present disclosure, which may be combined with the fourteenth aspect in combination with any other aspect listed herein unless specified otherwise, the at least one server includes at least one dedicated server or a cloud server.

In a nineteenth aspect of the present disclosure, which may be combined with any other aspect listed herein unless specified otherwise, a medical fluid delivery system includes: a medical fluid delivery machine configured to generate a message indicating that the medical fluid delivery machine is ready to perform a task; and at least one server in data communication with the medical fluid delivery machine via a first link to receive the message, the at least one server configured to (i) relay the message from the medical fluid delivery machine to a remote mobile communication device via a second link, (ii) receive a response from the remote mobile communication device indicating to start the task via the second link, and (iii) send a notification to the medical fluid delivery machine to start the task via the first link.

In a twentieth aspect of the present disclosure, which may be combined with the nineteenth aspect in combination with any other aspect listed herein unless specified otherwise, the first link is an internet link.

In a twenty-first aspect of the present disclosure, which may be combined with the nineteenth aspect in combination with any other aspect listed herein unless specified otherwise, the second link is an internet link or a cellular communications network link.

In a twenty-second aspect of the present disclosure, which may be combined with the nineteenth aspect in combination with any other aspect listed herein unless specified otherwise, the at least one server includes at least one dedicated server or a cloud server.

In a twenty-third aspect of the present disclosure, which may be combined with any other aspect listed herein unless specified otherwise, a mobile communication device includes: a first link to a first medical fluid delivery machine, the first link enabling the mobile communication device to receive a first message from the first medical fluid delivery machine indicating (i) that the first medical fluid delivery machine is ready to perform the same or a different task or (ii) a preprogrammed time for the first medical fluid delivery machine to perform a task; and a second link to a second medical fluid delivery machine, the second link enabling the mobile communication device to receive a second message from the second medical fluid delivery machine indicating (i) that the second medical fluid delivery machine is ready to perform the same or a different task or (ii) a preprogrammed time for the second medical fluid delivery machine to perform the same or a different task.

In a twenty-fourth aspect of the present disclosure, which may be combined with the twenty-third aspect in combination with any other aspect listed herein unless specified otherwise, the first and second links include first and second icons, respectively, on a screen of the mobile communication device, the first and second icons associated with the first and second medical fluid delivery machines, respectively.

In a twenty-fifth aspect of the present disclosure, which may be combined with the twenty-fourth aspect in combination with any other aspect listed herein unless specified otherwise, the first and second icons are associated with the first and second messages, respectively.

In a twenty-sixth aspect of the present disclosure, which may be combined with the twenty-fourth aspect in combination with any other aspect listed herein unless specified otherwise, at least one of the first or second icons is user selectable to view the first or second message, respectively.

In a twenty-seventh aspect of the present disclosure, which may be combined with the twenty-fourth aspect in combination with any other aspect listed herein unless specified otherwise, the first and second icons are arranged on the mobile communication device according to how the first and second medical fluid delivery machines are arranged at a facility.

In a twenty-eighth aspect of the present disclosure, which may be combined with the twenty-fourth aspect in combination with any other aspect listed herein unless specified otherwise, the mobile communication device includes at least one action icon that is user selectable to cause at least one of the first or second medical fluid delivery machines to perform the same or a different task.

In a twenty-ninth aspect of the present disclosure, which may be combined with the twenty-eighth aspect in combination with any other aspect listed herein unless specified otherwise, the at least one action icon is operated in combination with the first or second icons to select at least one of the first or second medical fluid delivery machines, respectively, to perform the same or a different task.

In a thirtieth aspect of the present disclosure, which may be combined with any other aspect listed herein unless specified otherwise, a medical fluid delivery system includes: a first medical fluid delivery device; a second medical fluid delivery device; a server in communication with the first and second medical fluid delivery devices; a software application for a mobile communication device, the software application causing a first icon to be displayed representing the first medical fluid delivery device and a second icon to be displayed representing the second medical fluid delivery device; a first communication link between the first and second medical fluid delivery devices and the server; and a second communication link between the server and the software application, the software application programmed to receive at least one status update from the first or second medical fluid delivery devices via the server and the first and second links.

In a thirty-first aspect of the present disclosure, which may be combined with the thirtieth aspect in combination with any other aspect listed herein unless specified otherwise, the first and second communication links are internet links.

In a thirty-second aspect of the present disclosure, which may be combined with the thirtieth aspect in combination with any other aspect listed herein unless specified otherwise, the software application is further programmed to send operational commands to the first and second medical fluid delivery machines via the server and the first and second links.

In a thirty-third aspect of the present disclosure, any of the structure and functionality disclosed in connection with FIGS. 1 to 9 may be combined with any other structure and functionality disclosed in connection with FIGS. 1 to 9.

In light of the present disclosure and the above aspects, it is therefore an advantage of the present disclosure to provide an improved medical fluid delivery system.

It is another advantage of the present disclosure to provide improved patient lifestyle.

It is a further advantage of the present disclosure to provide improved clinician or caregiver efficiency.

It is still another advantage of the present disclosure to provide improved machine efficiency.

It is still a further advantage of the present disclosure to provide improved patient compliance.

It is yet another advantage of the present disclosure to provide a medical fluid data transfer system and methodology that may be applied to different types of medical fluid delivery machines.

It is yet a further advantage of the present disclosure to provide a medical fluid data transfer system and methodology that enables communication between a medical fluid delivery machine and multiple people, such as a patient and clinician or patient and primary caregiver.

Moreover, it is an advantage of the present disclosure to reduce waste of disposable sets and other ancillary soft goods due to discards, which occur often when machine timers expire.

The advantages discussed herein may be found in one, or some, and perhaps not all of the embodiments disclosed herein. Additional features and advantages are described herein, and will be apparent from, the following Detailed Description and the figures.

DETAILED DESCRIPTION

The examples described herein are applicable to any medical fluid delivery system that delivers a medical fluid, such as blood, dialysis fluid, substitution fluid or and intravenous drug ("IV"). The examples are particularly well suited for kidney failure therapies, such as all forms of hemodialysis ("HD"), hemofiltration ("HF"), hemodiafiltration ("HDF"), continuous renal replacement therapies ("CRRT") and peritoneal dialysis ("PD"), referred to herein collectively or generally individually as renal failure therapy. The medical fluid delivery machines may alternatively be a drug delivery or nutritional fluid delivery device, such as a large volume peristaltic type pump or a syringe pump. The machines described herein may be used in home settings. For example, a machine operating with the data transfer regime of the present disclosure may be employed with a home HD machine, which can for example be run at night while the patient is sleeping. The medical fluid data transfer system and methodology of the present disclosure may alternatively be used to help clinicians or nurses in hospitals and/or clinics.

Figure 1:
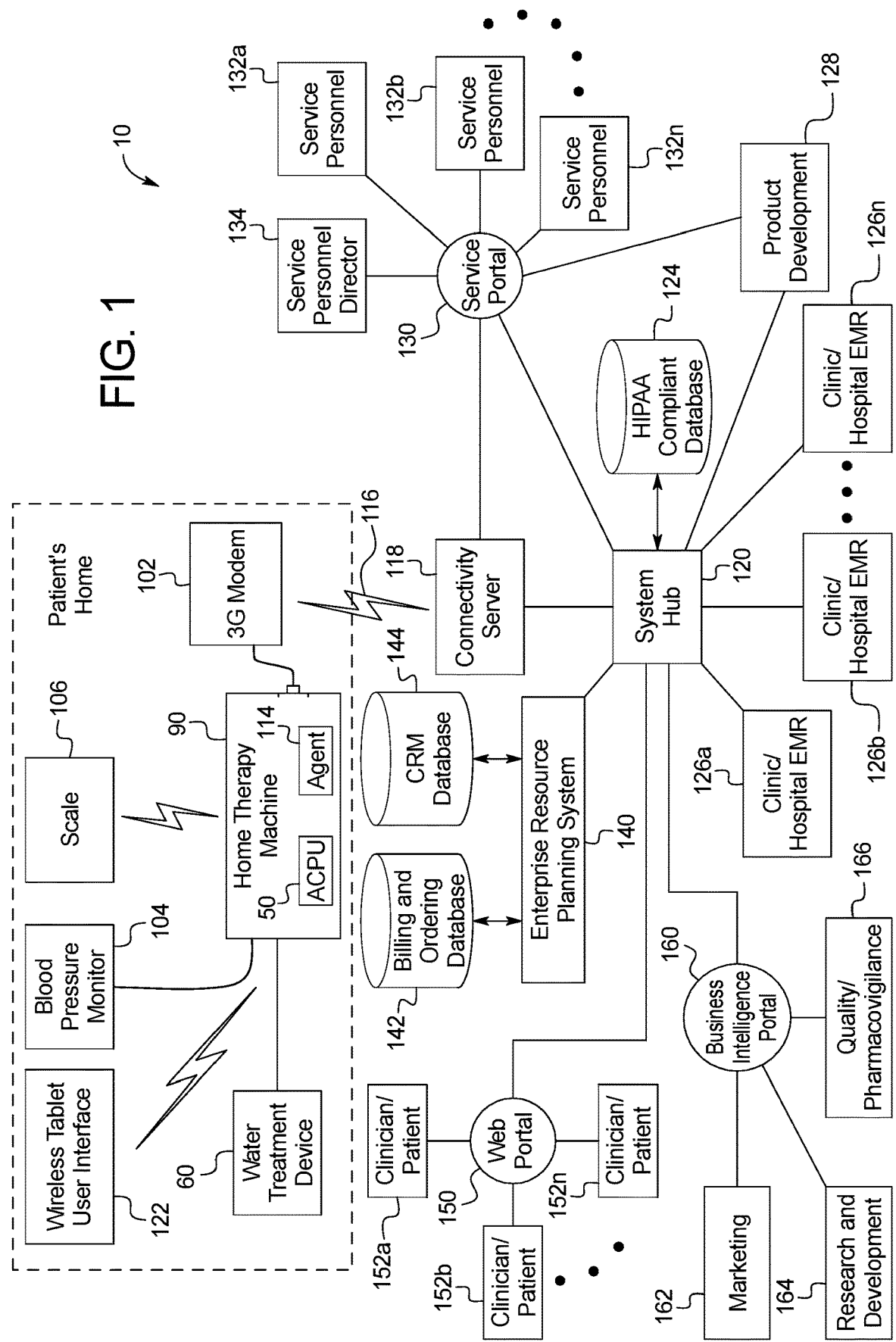
FIG. 1 is a schematic view illustrating one embodiment for a medical fluid data transfer system that incorporates the medical fluid delivery machines of the present disclosure, so that data may be transferred to and from such machines.

Referring now to the drawings and in particular to FIG. 1, a medical fluid data transfer system 10 is illustrated operating within a medical fluid delivery machine 90. System 10 incorporates many medical fluid delivery machines 90 (one type of which is discussed in detail below). Machines 90 of data transfer system 10 may be of a same type (e.g., all HD machines) or be of different types (e.g., a mix of HD, PD, CRRT, and medical or nutritional fluid delivery).

While a single medical fluid delivery 90 is illustrated as communicating with a connectivity server 118, system 10 oversees the operation of a plurality of medical fluid delivery systems and machines, of the same type or of different types listed above. For example, there may be M number of hemodialysis machines 90, N number of hemofiltration machines 90, O number of CRRT machines 90, P number of peritoneal dialysis machines 90, Q number of home drug delivery machines 90, and R number of nutritional or drug delivery machines 90 connected to server 118 and operating with system 10. The numbers M through R may be the same or different numbers, and may be zero, one, or more than one. In FIG. 1, medical fluid delivery machine 90 is illustrated as a home therapy machine 90 (the home indicated by dashed lines).

Home therapy machine 90 may receive at its front end purified water from a water treatment device 60 as discussed above. Water treatment device 60 connects to home therapy machine 90 via an Ethernet cable in an embodiment. Home therapy machines 90 in the illustrated embodiment operate with other devices besides water treatment device 60, such as a blood pressure monitor 104, a weigh scale, e.g., wireless weigh scale 106, and a user interface such as a wireless tablet user interface 122. Home therapy machine 90 connects to server 118 wirelessly in one embodiment via a modem 102. Each of these components may (but does not have to be) located within the patient's home, as demarcated by the dashed lines in FIG. 1. Any one, or more, or all of components 60, 104, 106 and 122 may communicate wired or wirelessly with home therapy machine 90. Wireless communication may be via Bluetooth™, WiFi™ Zigbee®, Z-Wave®, wireless Universal Serial Bus ("USB"), infrared, or any other suitable wireless communication technology. Alternatively, any one, or more or all of components 60, 104, 106 and 122 may communicate with home therapy machine 90 via wired communication.

Connectivity server 118 communicates with medical fluid delivery machine 90 via a medical device system hub 120. System hub 120 enables data and information concerning each home therapy machine 90 and its peripherals to travel back and forth via connectivity server 118 between machines 90 and the other clients connected to server 118. In the illustrated embodiment, system hub 120 is connected to a service portal 130, an enterprise resource planning system 140, a web portal 150, a business intelligence portal 160, a HIPAA compliant database 124, a product development team 128 and electronic medical records databases maintained for example at clinics or hospitals 126a to 126n.

Electronic medical records ("EMR") databases at clinics or hospitals 126a to 126n store electronic information concerning patients. System hub 120 may send the data collected from log files of machine 90 to hospital or clinic databases 126a to 126n to merge or supplement that patient's medical records. Databases at clinics or hospitals 126a to 126n may contain patient-specific treatment and prescription data and therefore access to such databases may be highly restricted. Enterprise resource planning system 140 obtains and compiles data generated via the patient and clinician website access, such as complaints, billing information and life cycle management information. Web portal 150 enables patients and clinics 152a to 152n treating the patients to access a website publicly available for users of medical fluid delivery machines 90. Business intelligence portal 160 collects data from system hub 120 and provides data to marketing 162, research and development 164, and quality/pharmacovigilance 166.

It should be appreciated that the systems, methods and procedures described herein may be implemented using one or more computer program or component. The programs of components may be provided as a series of computer instructions on any conventional computer-readable medium, including random access memory ("RAM"), read only memory ("ROM"), flash memory, magnetic or optical disks, optical memory, or other storage media. The instructions may be configured to be executed by a processor, which when executing the series of computer instructions performs or facilitates the performance of all or part of the disclosed methods and procedures.

In one embodiment, home therapy machine 90 performs a home treatment, such as home hemodialysis on a patient at the patient's home and then reports the results of that treatment to clinicians, doctors and nurses who are responsible for managing the health and well-being of that patient.

Home therapy machines 90 in an embodiment write log files using, e.g., a Linux™ operating system. The log files document pertinent home therapy machine 90 data, including peripheral device data. The log files may include any one or more of Extensible Markup Language ("XML"), comma-separated values ("CSV") or text files. The log files are placed into a file server box of the software of home therapy machine 90. It is also contemplated to store data at a peripheral device, e.g., water treatment device 60, which is not sent to machine 90. Such data may otherwise be obtained via the wired or wireless connection to the peripheral device or downloaded through other data connections or storage media. For example, a service person can access additional data via a laptop connected to water treatment device 60 or wireless weigh scale 106, e.g., via an Ethernet connection. Or, the additional data may be retrieved remotely from the peripheral devices, with home therapy machine 90 serving as the data transfer liaison between the peripheral device and authorized clients of medical fluid data transfer system.

In one embodiment, home therapy machine 90, e.g., via the internet, uses a connectivity service to transfer data between modem 102 and system hub 120. Here, a dedicated line may be provided at each patient's home for connecting the home therapy machine 90 to the connectivity server 118 via modem 102. Home therapy machine 90 in one embodiment accesses the internet using a separate, e.g., 3G, 4G or 5G, modem 102. Modem 102 may use an internet Service Provider ("ISP"), such as Vodafone™. In one implementation, a connectivity agent 114 developed by a connectivity service provider (e.g., provider of connectivity server 118) is installed onto the home therapy machine 90 and run on ACPU 50 of the machine. One suitable connectivity service is provided by Axeda™, which provides a secure managed connection 116 between medical devices and the connectivity server 118.

Connectivity agent 114 allows the home therapy machine 90 to connect to connectivity server 118 and transfer data to and from the connectivity server 118. The connectivity service operating via agent 114 and server 118 ensures that the connection with machine 90 is secure, ensures that the data correctly passes through machine 90's firewalls, checks whether there has been a data or system crash, and ensures that connectivity server 118 is communicating with the correct home therapy machine 90.

In one embodiment, home therapy machine 90 may only connect to connectivity server 118 when connectivity agent 114 is turned on or activated. During treatment and post-treatment disinfection, while machine 90 and its peripherals are functioning, connectivity agent 114 is turned off if one embodiment, which prevents home therapy machine 90 from communicating with any entity and sending or receiving data during treatment and disinfection or when machine 90 is live or running. When home therapy machine 90 is idle, e.g., after treatment and post-disinfection is complete, ACPU 50 turns connectivity agent 114 on in one embodiment. In an embodiment, connectivity agent 114 is off during treatment and possibly pretreatment. After treatment, connectivity agent 114 retrieves the log files from the home therapy machine 90 and transfers data to the connectivity server 118 using the connectivity service. The connectivity service routes data packets to their proper destination but in one embodiment does not modify, access, or encrypt the data.

In medical fluid data transfer system 10 system of FIG. 1, the connectivity service via connectivity server 118 may communicate data to various places via a system hub 120, such as a service portal 130, clinics or hospitals 126a to 126n, and a web portal 150. Connectivity server 118 allows service personnel 132a to 132n and/or clinicians to track and retrieve various assets across the network, such as appropriate home therapy machines 90 and 3G, 4G or 5G modem 102, and their associated information, including machine or modem serial numbers. Connectivity server 118 may also be used to receive and provide firmware upgrades, approved by a director of service personnel 134 and obtained remotely via service portal 130, to authorized home therapy machines 90 and associated peripherals, such as water treatment devices 60.

Figure 2:
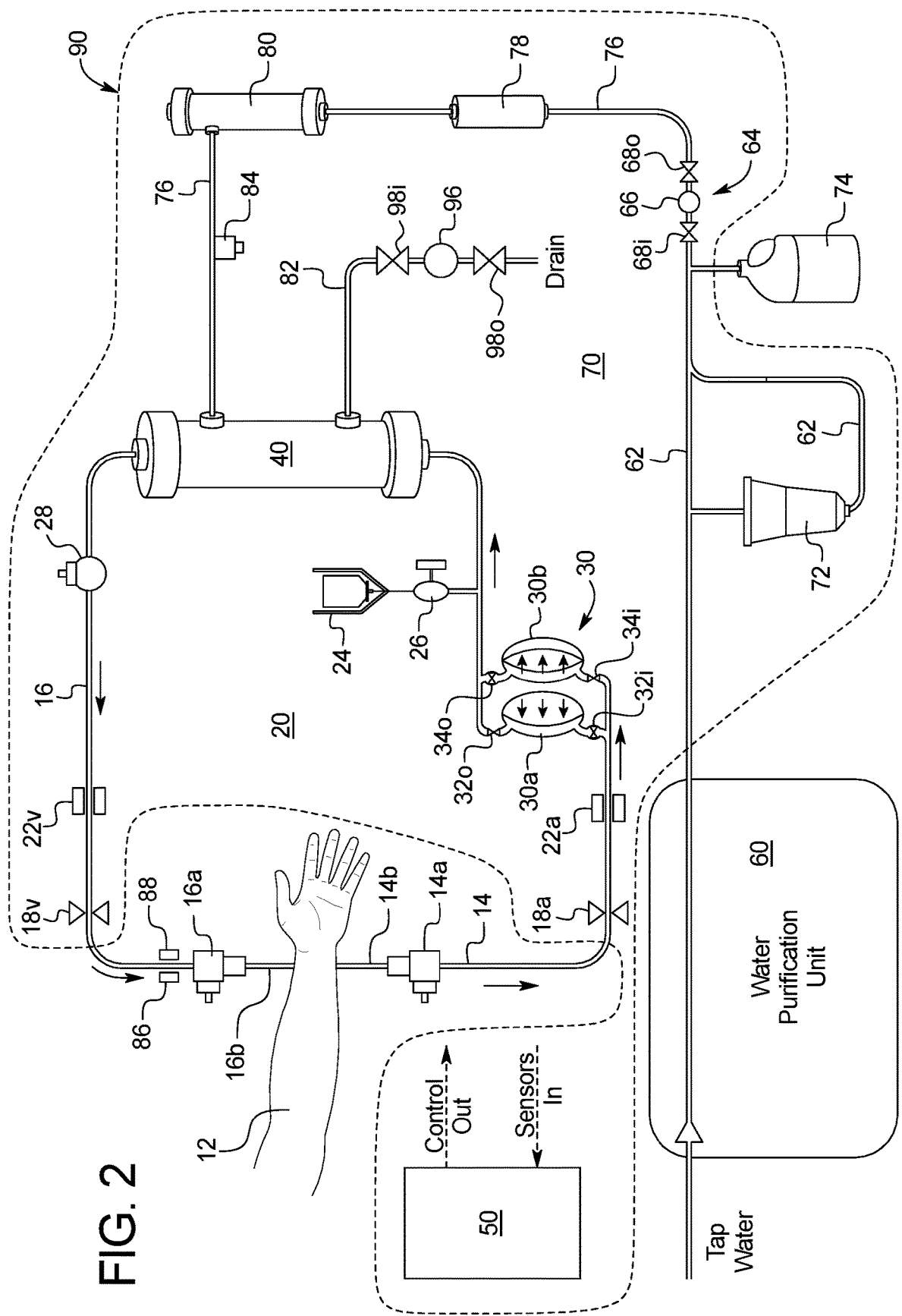
FIG. 2 is a schematic illustration of one embodiment of a medical fluid delivery machine of the present disclosure.

Referring now to FIG. 2, an example of an HD flow schematic for medical fluid delivery machine 90 is illustrated. Because the HD system of FIG. 2 is relatively complicated, FIG. 2 and its discussion also provide support for any of the renal failure therapy modalities discussed above and for an IV, drug delivery, or nutritional fluid delivery machine. Generally, medical fluid delivery machine 90 is shown having a simplified version of a dialysis fluid or process fluid delivery circuit. The blood circuit is also simplified but not to the degree that the dialysis fluid circuit is simplified. It should be appreciated that the circuits have been simplified to make the description of the present disclosure easier, and that the systems if implemented would have additional structure and functionality, such as is found in the publications incorporated by reference above.

Medical fluid delivery machine 90 of FIG. 2 includes a blood circuit 20. Blood circuit 20 pulls blood from and returns blood to a patient 12. Blood is pulled from patient 12 via an arterial line 14, and is returned to the patient via a venous line 16. Arterial line 14 includes an arterial line connector 14a that connects to an arterial needle 14b, which is in blood draw communication with patient 12. Venous line 16 includes a venous line connector 16a that connects to a venous needle 16b, which is in blood return communication with the patient. Arterial and venous lines 14 and 16 also include line clamps 18a and 18v, which can be spring-loaded, fail-safe mechanical pinch clamps. Line clamps 18a and 18v are closed automatically in an emergency situation in one embodiment.

Arterial and venous lines 14 and 16 also include air or bubble detectors 22a and 22v, respectively, which can be ultrasonic air detectors. Air or bubble detectors 22a and 22v look for air in the arterial and venous lines 14 and 16, respectively. If air is detected by one of air detectors 22a and 22v, system 10 closes line clamps 18a and 18v, pauses the blood and dialysis fluid pumps, and provides instructions to the patient to clear the air so that treatment can resume.

A blood pump 30 is located in arterial line 14 in the illustrated embodiment. In the illustrated embodiment, blood pump 30 includes a first blood pump pod 30a and a second blood pump pod 30b. Blood pump pod 30a operates with an inlet valve 32i and an outlet valve 32o. Blood pump pod 30b operates with an inlet valve 34i and an outlet valve 34o. In an embodiment, blood pump pods 30a and 30b are each blood receptacles that include a hard outer shell, e.g., spherical, with a flexible diaphragm located within the shell, forming a diaphragm pump. One side of each diaphragm receives blood, while the other side of each diaphragm is operated by negative and positive air pressure. Blood pump 30 is alternatively a peristaltic pump operating with the arterial line 14 or multiple peristaltic pumps operating with arterial line 14 and venous line 16.

A heparin vial 24 and heparin pump 26 are located between blood pump 30 and blood filter 40 (e.g., dialyzer) in the illustrated embodiment. Heparin pump 26 may be a pneumatic pump or a syringe pump (e.g., stepper motor driven syringe pump). Supplying heparin upstream of blood filter 40 helps to prevent clotting of the filter's membranes.

A primary control processor ("ACPU") or control unit control unit 50 includes one or more processor and memory. Control unit 50 receives air detection signals from air detectors 22a and 22v (and other sensors of system 10, such as temperature sensors, blood leak detectors, conductivity sensors, pressure sensors, and access disconnection transducers 86, 88), and controls components such as line clamps 18a and 18v, blood pump 30, heparin pump 26, dialysis fluid pumps 64 and 96, and valves 32i, 32o, 34i, 34o, 68i, 68o, 98i and 98o. Blood exiting blood filter 40 via venous line 16 flows through an airtrap 28. Airtrap 28 removes air from the blood before the dialyzed blood is returned to patient 12 via venous line 16.

With the hemodialysis version of medical fluid delivery machine 90 of FIG. 2, dialysis fluid is pumped along the outside of the membranes of blood filter 40, while blood is pumped through the insides of the blood filter membranes. Dialysis fluid is prepared beginning with the purification of water via a water purification unit 60. One suitable water purification unit is set forth in U.S. Patent Publication No. 2011/0197971, entitled, "Water Purification System and Method", filed Apr. 25, 2011, the entire contents of which are incorporated herein by reference and relied upon. In one embodiment, water purification unit includes filters and other structures to purify tap water (e.g., remove pathogens and ions such as chlorine), so that the water is in one implementation below 0.03 endotoxin units/ml ("EU/ml") and below 0.1 colony forming units/ml ("CFU/ml"). Water purification unit 60 may be provided in a housing separate from the housing or chassis of the hemodialysis machine 90, which includes blood circuit 20 and dialysis fluid circuit 70.

Dialysis fluid circuit 70 is again highly simplified in FIG. 2 to ease illustration. Dialysis fluid circuit 70 in actuality may include all of the relevant structure and functionality set forth in the publications incorporated by reference above. Certain features of dialysis fluid circuit 70 are illustrated in FIG. 2. In the illustrated embodiment, dialysis fluid circuit 70 includes a to-blood filter dialysis fluid pump 64. Pump 64 is in one embodiment configured the same as blood pump 30. Pump 64, like pump 30, includes a pair of pump pods 66 each having inlet valves 68i and outlet valves 68o, which again may be spherically configured. The two pump pods, like with blood pump 30, are operated alternatingly so that one pump pod is filling with HD dialysis fluid, while the other pump pod is expelling HD dialysis fluid.

Pump 64 is a to-blood filter dialysis fluid pump. There is another dual pod pump chamber 96 operating with valves 98i and 98o located in drain line 82 to push used dialysis fluid to drain. There is a third pod pump (not illustrated) for pumping pump purified water through a bicarbonate cartridge 72. There is a fourth pod pump (not illustrated) used to pump acid from acid container 74 into mixing line 62. The third and fourth pumps, the concentrate pumps, may be single pod pumps because continuous pumping is not as important in mixing line 62 due to a buffering dialysis fluid tank (not illustrated) between mixing line 62 and to-blood filter dialysis fluid pump 64 in one embodiment.

A fifth pod pump (not illustrated) provided in drain line 82 is used to remove a known amount of ultrafiltration ("UF") when an HD therapy is provided. System 10 keeps track of the UF pump to control and know how much ultrafiltrate has been removed from the patient. System 10 ensures that the necessary amount of ultrafiltrate is removed from the patient by the end of treatment.

Each of the above-described pumps may alternatively be a peristaltic pump operating with a pumping tube. If so, the system valves may still be actuated pneumatically according to the features of the present disclosure.

In one embodiment, purified water from water purification unit 60 is pumped along mixing line 62 though bicarbonate cartridge 72. Acid from container 74 is pumped along mixing line 62 into the bicarbonated water flowing from bicarbonate cartridge 72 to form an electrolytically and physiologically compatible dialysis fluid solution. The pumps and temperature-compensated conductivity sensors used to properly mix the purified water with the bicarbonate and acid are not illustrated but are disclosed in detail in the publications incorporated by reference above.

FIG. 2 also illustrates that dialysis fluid is pumped along a fresh dialysis fluid line 76, through a heater 78 and an ultrafilter 80, before reaching blood filter 40, after which used dialysis fluid is pumped to drain via drain line 82. Heater 78 heats the dialysis fluid to body temperature or about 37° C. Ultrafilter 80 further cleans and purifies the dialysis fluid before reaching blood filter 40, filtering foreign matter and/or contaminants introduced for example via bicarbonate cartridge 72 or acid container 74 from the dialysis fluid.

Dialysis fluid circuit 70 also includes a sample port 84 in the illustrated embodiment. Dialysis fluid circuit 70 will further include a blood leak detector (not illustrated but used to detect if a blood filter 40 fiber is torn) and other components that are not illustrated, such as balance chambers, plural dialysis fluid valves, and a dialysis fluid holding tank, all illustrated and described in detail in the publications incorporated by reference above.

In the illustrated embodiment, medical fluid delivery machine 90 is an online, pass-through system that pumps dialysis fluid through blood filter one time and then pumps the used dialysis fluid to drain. Both blood circuit 20 and dialysis fluid circuit 70 may be hot water disinfected after each treatment, such that blood circuit 20 and dialysis fluid circuit 70 may be reused. In one implementation, blood circuit 20 including blood filter 40 is hot water disinfected and reused daily for about one month, while dialysis fluid circuit 70 is hot water disinfected and reused for about six months.

In alternative embodiments, for CRRT for example, multiple bags of sterilized dialysis fluid or infusate are ganged together and used one after another. In such a case, the emptied supply bags can serve as drain or spent fluid bags.

Medical fluid delivery machine 90 includes an enclosure as indicated by the dashed line of FIG. 2. The enclosure of machine 90 varies depending upon the type of treatment, whether the treatment is in-center or a home treatment, and whether the dialysis fluid/infusate supply is a batch-type (e.g., bagged) or on-line.

Figure 3:
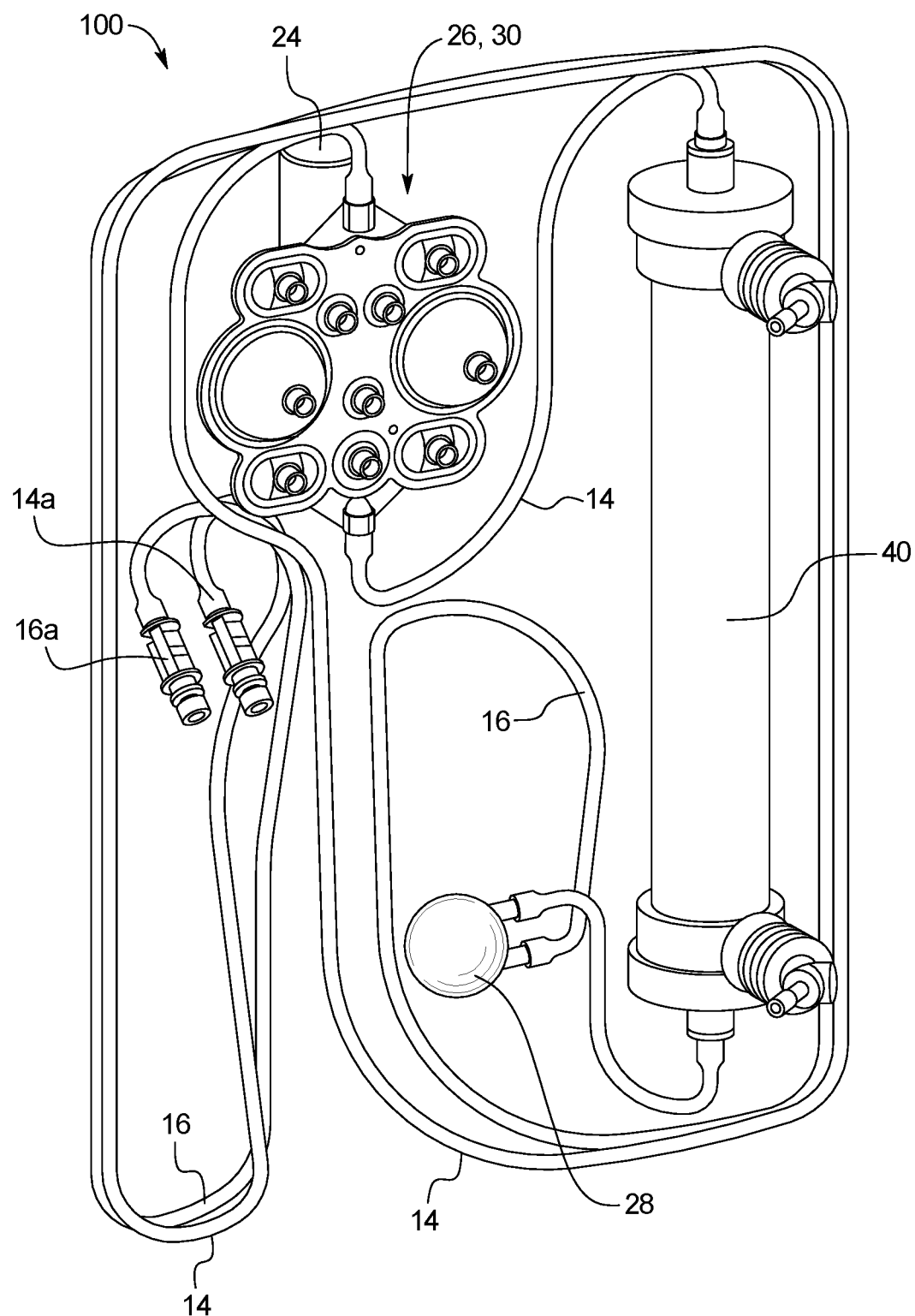
FIG. 3 is a perspective view illustrating a blood set for use with one embodiment of the medical fluid delivery machine of FIG. 2.

FIG. 3 illustrates that machine 90 of FIG. 2 may operate with a blood set 100. Blood set 100 includes arterial line 14, venous line 16, heparin vial 24, heparin pump 26/blood pump 30 and blood filter 40 (e.g., dialyzer). An airtrap 28 may be located in venous line 16 to remove air from the blood before being returned to patient 12. Air detectors 22*a* and 22*v* contact arterial and venous lines 14 and 16, respectively, for operation.

In FIGS. 2 and 3, any of pumps 26, 30 (30*a* and 30*b*), 64, 96 (and other pumps not illustrated) and any of the valves, such as valves 32*i*, 32*o*, 34*i*, 34*o*, 68*i*, 68*o*, 98*i*, and 98*o* may be pneumatically actuated. In an embodiment, each of the pumps and valves has a fluid side and an air side, separated by a flexible membrane. Negative pneumatic pressure may be applied to the air side of the membrane to draw fluid into a pump chamber or to open a valve (or the pump or valve could be opened by venting positive closing pressure to atmosphere and allowing fluid pressure to open). Positive pneumatic pressure is applied to the air side of the membrane to expel fluid from a pump chamber or to close a valve.

Figure 4:
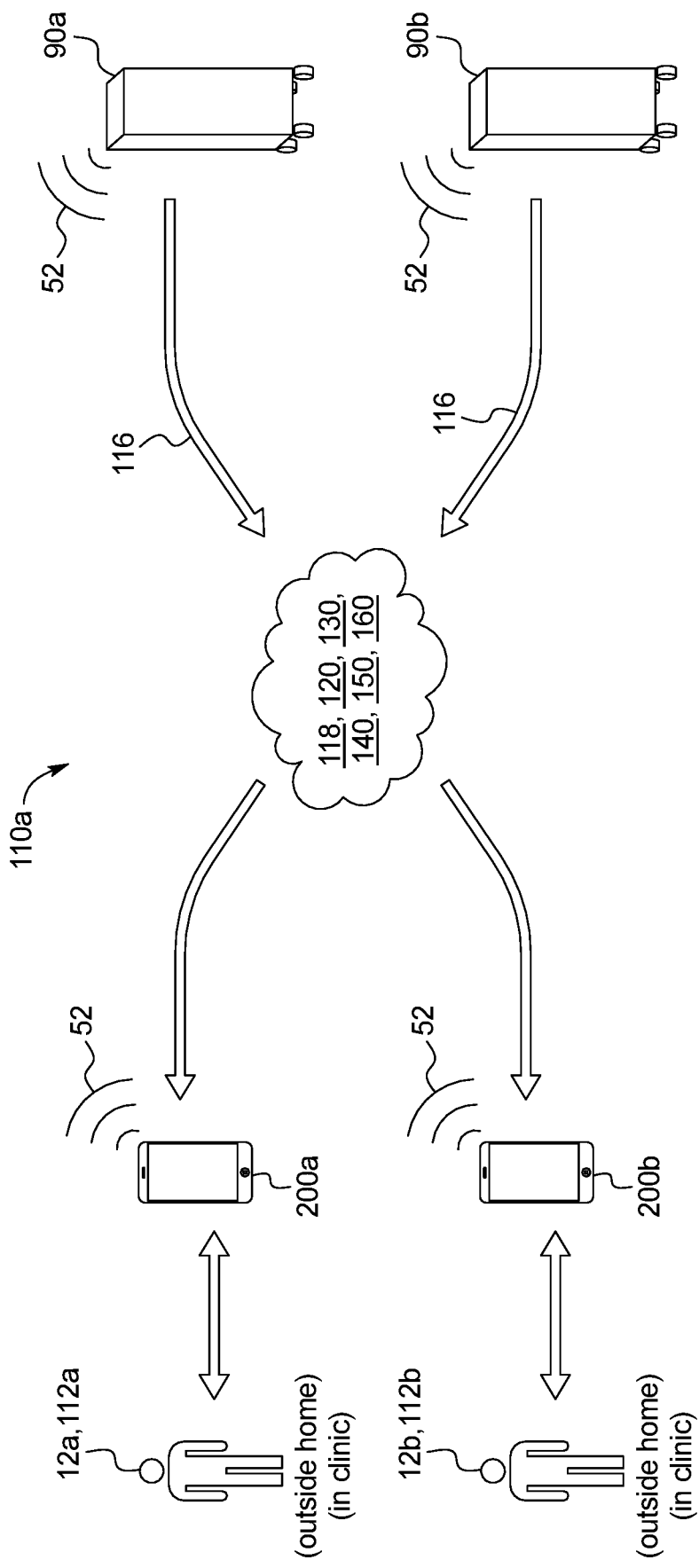
FIG. 4 is a schematic view of one embodiment for a medical fluid delivery machine and data transfer system and method of the present disclosure.

Referring now to FIG. 4, a system 110*a* of the present disclosure is illustrated. System 110*a* in the illustrated embodiment operates with system 10 described above, including connectivity server 118, system hub 120, service portal 130, enterprise resource planning system 140, web portal 150, and business intelligence portal 160, which are illustrated in FIG. 4 as being part of a cloud environment. Connectivity server 118, system hub 120, service portal 130, enterprise resource planning system 140, web portal 150, and business intelligence portal 160 may each be part of a cloud environment or be located at one or more dedicated server.

Other components of system 10 not illustrated in FIG. 4 may also be part of system 110*a*. For instance, medical fluid delivery machines 90*a* and 90*b* may reside separately in the homes of patients 12*a* and 12*b* (who are illustrated as being outside the home). Alternatively, medical fluid delivery machines 90*a* and 90*b* may reside in the same clinic 126*a* to 126*n* or in different ones of clinics 126*a* to 126*n*. Clinicians 112*a* and 112*b* may reside inside or outside of the clinics.

Medical fluid delivery machines 90*a* and 90*b* are connected to connectivity server 118 via secure managed connections 116 as described above. To do so, machines 90*a* and 90*b* connect to internet 52, e.g., via modems 102 discussed above. System hub 120 in one embodiment stores middleware software that may be accessed by mobile communication devices 200*a* and 200*b* (referred to herein collectively as devices 200 or generally individually as device 200). Mobile communication devices 200*a* and 200*b* may be smartphones, for example, running on Android™, iOS™, Windows Phone™, BlackBerry™ Sailfish OS™, Tizen™, or Ubuntu Touch™ operating systems. Mobile communication devices 200*a* and 200*b* may belong to patients 12*a* and 12*b*, respectively, and/or clinicians 112*a* and 112*b*, respectively. Mobile communication devices 200*a* and 200*b* as illustrated in FIG. 4 are also connected to internet 52.

In one embodiment, mobile communication devices 200*a* and 200*b* download application software ("app") from middleware software stored on system hub 120 via their connection to internet 52. The app is updated whenever there is a change of state of the corresponding machine 90*a* or 90*b*. For example, medical fluid delivery machine 90*a* may have just completed its automated self-test routine and is now ready to run a disinfection procedure. Machine 90*a* may generate a code identifying this state and send it to middleware software stored on system hub 120. Middleware software then translates the code into a message, e.g., using a look-up table, such as, "self-test completed, ready for disinfection" and cause the app downloaded onto mobile communication device 200*a* of patient 12*a* or clinician 112*a* to display the message. The app may be programmed to provide a visual identifier along with the message, such as, an icon that is associated with the particular state in which machine 90*a* resides. The app may also provide any one or more of an audio alert, such as a "ding" sound, and/or a haptic alert, such as a vibration, which prompt patient 12*a* or clinician 112*a* to view the app and see the state change of machine 90.

In another example, medical fluid delivery machine 90*b* may have been preprogrammed to begin treatment at 3:00 PM. Medical fluid delivery machine 90*b* may need three hours for self-test and disinfection. Patient 12*a* or clinician 112*a* therefore needs to be at machine 90*b* by noon to start pre-treatment. In an embodiment, patient 12*a* or clinician 112a makes a setting on machine 90b as to how soon before the three hour preparation time that the patient 12a or clinician 112a should be notified or alerted, e.g., two hours. So in this example, machine 90b may generate a code at 10:00 AM and send the code to middleware software stored on system hub 120. Middleware software then translates the code into a message, e.g., using a look-up table, such as, "treatment preparation needs to start in two hours" and cause the app downloaded onto mobile communication device 200b of patient 12b or clinician 112b to display the message. The app may again be programmed to provide a visual identifier along with the message, such as, a countdown timer that counts down from one-hundred-twenty minutes to a timeout at zero. The app may also provide any one or more of an audio alert, such as a "ding" sound, and/or a haptic alert, such as a vibration, which prompt patient 12b or clinician 112b to view the app and see the treatment preparation notification. The app may also be programmed to repeat the "ding" sound and/or haptic feedback at preprogrammed intervals during the countdown period, e.g., at an hour and at thirty minutes.

In addition or alternatively to providing the app on the user's communication device 200b, it is contemplated for the middleware software at system hub 120 to convert the code from machine 90b into a message that is lodged onto device 200's native task tracking feature, such as its calendar application. Most smartphone devices 200, for example, are provided with a calendar that separates each day into time segments, such as hours. Here, the message converted by middleware software of system hub 120 may be programmed to access the calendar of authorized communication device 200b and to populate the appropriate time segment of the appropriate day with the appropriate information. In the above example, for the appropriate day, the native calendar software application will have its 10:0:00 AM timeslot filled with a message, such as, "treatment preparation needs to start in two hours". An audio and/or haptic feedback signal may be provided to notify patient 12 or clinician 112 about the calendar entry.

It should be appreciated that machines 90a and 90b, middleware software at central server 120, and communication devices 200a and 200b, may be programmed and operated as described above to provide any desired message to patients 12a, 12b and/or clinicians 112a, 112b and are not limited to the messages described herein. For example, patients 12a, 12b and/or clinicians 112a, 112b may be likewise informed at the end of disinfection with an accompanying countdown timer that treatment needs to start within the countdown time to avoid having to re-disinfect machine 90a, 90b.

Figure 5:
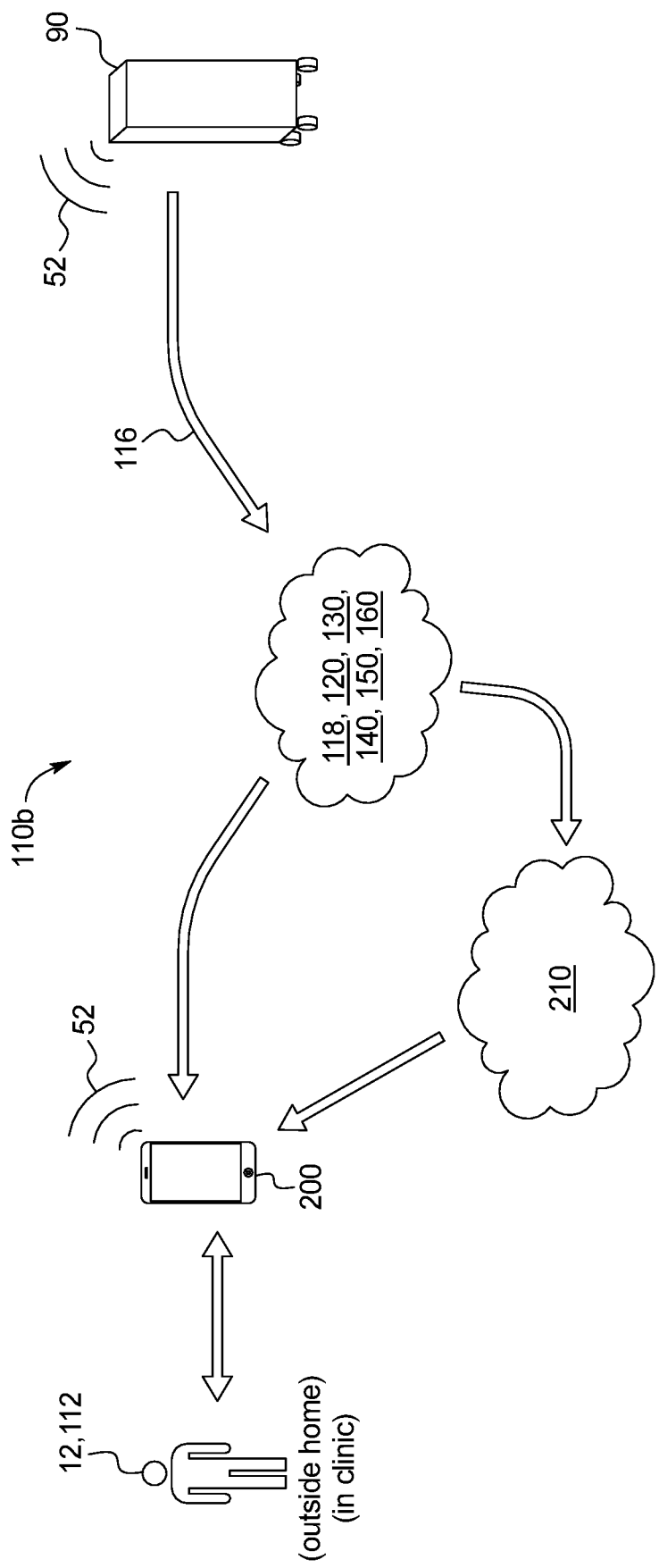
FIG. 5 is a schematic view of a second embodiment for a medical fluid delivery machine and data transfer system and method of the present disclosure.

Referring now to FIG. 5, a system 110b of the present disclosure is illustrated. System 110b in the illustrated embodiment operates with system 10 described above, including connectivity server 118, system hub 120, service portal 130, enterprise resource planning system 140, web portal 150, and business intelligence portal 160, which are illustrated in FIG. 5 as being part of a cloud environment, but may be located alternatively at one or more dedicated server. Other components of system 10 not illustrated in FIG. 5 may also be part of system 110a. A single medical fluid delivery machine 90 is illustrated for ease of description, however, multiple medical fluid delivery machines 90 may be likewise connected to system 110b. Medical fluid delivery machine 90 may reside in the home of patient 12 (illustrated as being outside the home) or in a clinic 126a to 126n for clinician 112. Medical fluid delivery machine 90 is connected again to connectivity server 118 via secure managed connection 116 and an internet 52 connection using, e.g., modem 102 in the illustrated embodiment.

System hub 120 in one embodiment stores middleware software that may be accessed by mobile communication device 200 (shown as single device for ease, but multiple devices 200 may be likewise connected to system 110b). Mobile communication devices 200 in FIG. 5 include all of the structure, functionality and alternatives disclosed for devices 200a and 200b illustrated in FIG. 4, including being connected to internet 52. In FIG. 5, mobile communication device 200 may, but does not have to, download a software application ("app") from middleware software stored on system hub 120 via their connection to internet 52. The app may be operated exactly as described above in connection with FIG. 4, including middleware software converting a coded message from machine 90 into a format presentable on the app. Alternatively or additionally, middleware software stored on system hub 120 may be able to convert the code from machine 90 into a message that is lodged onto mobile communication device 200's native task tracking feature, such as its calendar application, in any of the ways described in FIG. 4.

Further alternatively or additionally, system 110b includes a cellular network 210 that interfaces between middleware software, e.g., stored at system hub 120, and mobile communication device 200. Cellular network 210 may include a network of cellular phone towers operating using radio waves and/or employ a satellite. Communication protocols suitable for use with cellular network 210 of system 110b may be long range protocols, such as (i) the "worldwide interoperability for microwave access" ("WiMAX") protocol; and (ii) the "global system for mobile communications" ("GSM") protocol, which is a widespread long-range wireless protocol enabling data communication to the many of the world's cellular telephones. Network 210 may alternatively or additionally employ a medium range protocol, such as a wireless local area network ("WLAN"), which can be a protocol that is part of the Institute of Electrical & Electronics Engineers ("IEEE") 802.11 standard, such as (i) IEEE 802.11a, (ii) IEEE 802.11b, (iii) WEE 802.11g, or (iv) 802.11n. Other suitable cellular technologies may include CDMA, AMPS (analog), General Packet Radio Service ("GPRS"), cdmaOne, CDMA2000, Evolution-Data Optimized ("EV-DO"), Enhanced Data Rates for GSM Evolution ("EDGE"), Universal Mobile Telecommunications System ("UMTS"), Digital Enhanced Cordless Telecommunications ("DECT"), Digital AMPS ("IS-136/TDMA"), and Integrated Digital Enhanced Network ("iDEN").

Mobile communication devices 200 communicate with cellular network 210 via any of the ways known to those of skill, e.g., via Short Messaging Service ("SMS") or Multimedia Messaging Service ("MMS") protocols. Middleware software at system hub 120 may communicate with cellular network 210 in a number of ways. In one example, the phone numbers and carriers of users 12, 112 (any or all of patient 12, patient's at home care partner, patient's clinician 112) are associated, e.g., via a look-up table at middleware software, with a specific machine 90. When a message/code from a specific machine 90 is received by middleware, middleware software may be programmed to send an email to [user phone number]@[carrier].net. For example, if patient 001's phone number is (555) 555-5555 and patient 001's carrier is AT&T™, when patient 001's machine 90 sends a message to middleware software of system hub 120, upon receipt, middleware software 120 is programmed to relay an email to 5555555555@att.net, which is received by patient 001's mobile communication device 200 as a text message. Those of skill in the art understand that there are multiple websites devoted to informing how to email to a text message, outlining the specifics required by different carriers.

Middleware software stores each of the telephone numbers of each of mobile communication devices 200 and matches each of those numbers with a machine 90. When an event code is sent from a machine 90 to middleware software as has been described above, middleware software locates the telephone number of the mobile communication device 200 associated with that machine, converts the code to an appropriate message, e.g., using a look-up table as described above, and sends the converted message to the recalled telephone number. It is contemplated that multiple communication devices 200 may be associated with the same medical fluid delivery machine 90. For example, in any of clinics 126a to 126n, multiple doctor, nurse and/or clinician telephone numbers may be associated with the same machine 90. In a home environment, the telephone numbers for patient 12 and his or her clinician and/or caregiver assistant may be associated with the same machine 90.

Likewise, a telephone number for a mobile communication device 200 may be associated with multiple medical fluid delivery machines 90. For example, in any of clinics 126a to 126n, a single nurse may monitor multiple machines 90. If an event occurs to any of those machines during the nurse's shift, the nurse may be notified via a cellular message sent to the nurse's mobile communication device 200. This scenario is described in detail below in connection with FIGS. 7 to 9.

The cellular messages may convey in formation concerning any of the same events discussed above for the software app and calendar updating modes of populating mobile communication devices 200 with information. For example, medical fluid delivery machine 90 may have just completed its automated self-test routine and is now ready to run a disinfection procedure. Machine 90 may generate a code identifying this state and send it to middleware software stored on system hub 120. Middleware software then translates the code into a message, e.g., using a look-up table, such as, "self-test completed, ready for disinfection" and cause the cellular output routine discussed above for example to send a text message to mobile communication device 200 of patient 12 or clinician 112 to display the message. In an alternative embodiment, a code is not needed and machine 90 instead sends an actual text string, which middleware software forwards on to the mobile communication device 200 as a text message via the cellular output routine discussed above for example. As is known, the receipt of the text message on communication device 200 may be accompanied with an audio, e.g., "ding" sound, and/or a haptic alert, such as a vibration, which prompt patient 12 or clinician 112 to view the message.

In another example, medical fluid delivery machine 90 may have been preprogrammed to begin treatment at 3:00 PM. Medical fluid delivery machine 90 may again need three hours for self-test and disinfection. Patient 12 or clinician 112 therefore needs to be at machine 90 by noon to start pre-treatment. In an embodiment, patient 12 or clinician 112 makes a setting on machine 90 as to how soon before the three hour preparation time that patient 12 or clinician 112 should be notified or alerted, e.g., two hours. Here, machine 90 generates a code at 10:00 AM and sends the code to middleware software stored on system hub 120. Middleware software then translates the code into a message, e.g., using a look-up table, such as, "treatment preparation needs to start in two hours" and cause the cellular output routine discussed above for example to send a text message to mobile communication device 200 of patient 12 or clinician 112 to display the message, e.g., along with an audio alert, such as a "ding" sound, and/or a haptic alert, such as a vibration, which prompt patient 12 or clinician 112 to view the notification.

It should be appreciated that machine 90, middleware software at central server 120, and communication device 200 may be programmed and operated as described above to provide any desired message to patients 12 and/or clinicians 112 using cellular network 210 alternatively or additionally. For example, patients 12 and/or clinicians 112 may be likewise informed at the end of disinfection that treatment needs to start within the countdown time to avoid having to re-disinfect machine 90. It should also be appreciated that the updating of the native task tracking features, such as the calendar application of communication device 200 may be done over an internet connection or via cellular network 210 illustrated in FIG. 5.

Figure 6:
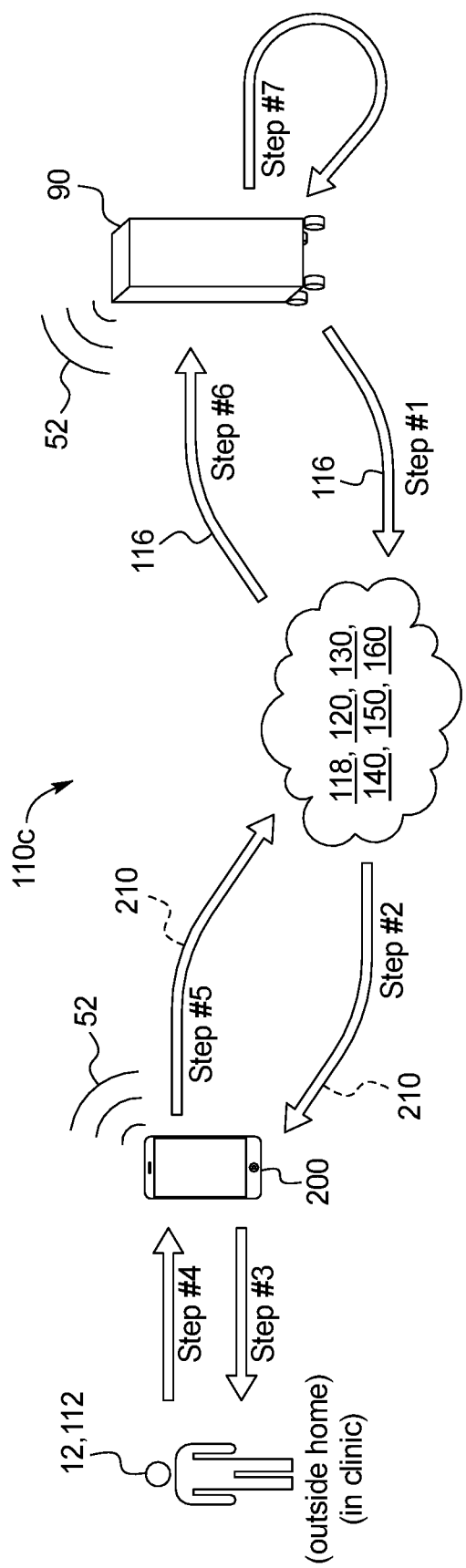
FIG. 6. is a schematic view of a third embodiment for a medical fluid delivery machine and data transfer system and method of the present disclosure.

Referring now to FIG. 6, a system 110c of the present disclosure is illustrated. System 110c in the illustrated embodiment operates with system 10 described above, including connectivity server 118, system hub 120, service portal 130, enterprise resource planning system 140, web portal 150, and business intelligence portal 160, which are illustrated in FIG. 6 as being part of a cloud environment, but may be located alternatively at one or more dedicated server. Other components of system 10 not illustrated in FIG. 6 may also be part of system 110a. A single medical fluid delivery machine 90 is illustrated for ease of description, however, multiple medical fluid delivery machines 90 may be likewise connected to system 110b. Medical fluid delivery machine 90 may reside in the home of patient 12 (illustrated as being outside the home) or in a clinic 126a to 126n for clinician 112. Medical fluid delivery machine 90 is connected again to connectivity server 118 via secure managed connection 116 and an internet 52 connection using, e.g., modem 102 in the illustrated embodiment. In FIG. 6, connectivity server 118 and secure managed connection 116 are used for two-way communication.

System hub 120 in one embodiment stores middleware software that may be accessed by mobile communication device 200 (shown as single device for ease, but multiple devices 200 may be likewise connected to system 110b). Mobile communication devices 200 in FIG. 6 include all of the structure, functionality and alternatives disclosed for devices 200a and 200b illustrated in FIG. 4, including being connected to internet 52. In FIG. 6, mobile communication device 200 may, but does not have to, download a software application ("app") from middleware software stored on system hub 120 via their connection to internet 52. The app may be operated exactly as described above in connection with FIG. 4, including middleware software converting a coded message from machine 90 into a format presentable on the app. Alternatively or additionally, middleware software stored on system hub 120 may be able to convert the code from machine 90 into a message that is lodged onto mobile communication device 200's native task tracking feature, such as its calendar application, in any of the ways described in FIG. 4. The calendar application may alternatively be updated via a cellular network 210 (illustrated as an alternative via dashed lead lines in FIG. 6) discussed above in connection with FIG. 5.

FIG. 6 illustrates that communication may be two-way between medical fluid delivery machines 90 and mobile communication devices 210. Communication between mobile communication devices 210 and middleware software at server computer 120 may be via internet 52 and/or cellular network 210. Communication between middleware software at server computer 120 may be via connectivity server 118 via secure managed connection 116 as described in detail above.

As discussed above, home therapy machine 90 connects to connectivity server 118 via its onboard connectivity agent 114, which in one embodiment is turned off during treatment (may or may not be turned off during post-treatment disinfection), e.g., while machine 90 and its peripherals are functioning. This prevents home therapy machine 90 from communicating with any entity and sending or receiving data during treatment and disinfection or when machine 90 is live or running. It is contemplated that the communication via systems 110a to 110c be protected in the same way. For instance, suppose that a particular machine 90 is set via the middleware software to communicate with both patient 12 and clinician 112. Here, if patient is being treated by machine 90, it is contemplated that connectivity agent 114 be shut off so that clinician 112 at that time cannot receive notifications from or send commands to that machine 90. In an alternative embodiment, clinician 112 may be able to receive notifications machine 90 during treatment.

Determining when to disconnect connectivity agent 114 (no communication) may be dependent upon what or how many machine states that systems 110a to 110c desire to communicate to mobile communication devices 200. For instance, suppose that it is only desired to inform patient 12 or clinician 112 two hours before treatment preparation that the patient 12 or clinician 112 needs to return to machine 90 to start treatment preparation. Here, connectivity agent 114 may be turned off as soon as patient 12 or clinician 112 begins the first treatment preparation step, e.g., running self-test routine.

In another example, it may be desired for machine 90 to run the self-test routine automatically at some preset time before treatment is set to start. Machine 90 notifies patient 12 or clinician 112 when it is time to begin disinfection. Here, connectivity agent 114 may be disconnected once patient 12 or clinician 112 begins the machine disinfection. In a further example, it may be desired for machine 90 to notify patient 12 when disinfection is complete so that the patient begins treatment within a certain amount of time from the end of disinfection, so that disinfection does not need to be repeated. Here, connectivity agent 114 may be disconnected once patient 12 or clinician 112 begins treatment, e.g., upon the beginning of prime in which the patient is still yet to be connected to treatment lines, e.g., to arterial line 14 or venous line 16.

System 110c allows patient 12 or clinician 112 to begin any of the above actions (and others not expressly described herein) remotely. Patient 12 or clinician 112 may for example select an icon on the app displayed on mobile communication device 200 to begin, e.g., the self-test routine or a disinfection procedure. The selection of the icon is transmitted over internet 52 to middleware software. Middleware software may then for example translate, e.g., via a look-up table, the icon selection into an action code that is sent via connectivity server 118 and secure managed connection 116 to machine 90 whose connectivity agent 114 is on, allowing the action code for the selected action to be sent to the machine's ACPU 50, which begins the performance of the selected action.

In an alternative embodiment, patient 12 or clinician 112 may for example enters a known code in a text message selecting a particular action to be performed at machine 90, e.g., the self-test routine or a disinfection procedure. The code may be a suggestive code, such as "self-test" or "disinfection". The text message is sent via cellular network 210 to middleware software at system hub 120. Middleware software converts, e.g., via a look-up table, the texted code into an action code for the selected action. Or, the code entered by patient 12 or clinician 112 may be the action code, so that no conversion is needed. In either case, the action code is sent via connectivity server 118 and secure managed connection 116 to machine 90 whose connectivity agent 114 is on, allowing the action code for the selected action to be sent to the machine's ACPU 50, which begins the performance of the selected action.

FIG. 6 illustrates the following example seven step sequence. In step 1, medical fluid delivery machine 90 sends a message to middleware software application at system hub 120 indicating that the machine is ready for patient 12 to initiate the start of machine 90's, e.g., two hour, automated self-test routine. In step 2, the middleware software application at system hub 120 sends a corresponding, e.g., translated, message to the patient's mobile communication device 200 indicating that machine 90 is ready for patient 12 to initiate the start of the automated self-test routine.

In step 3, a custom app downloaded to the patient's mobile communication device 200 alerts patient 12 via an audio, visual and/or haptic alert and associated message that patient 12's machine 90 is ready for the patient to initiate the start of the, e.g., two hour, automated self-test routine. In step 4, patient 12 uses the custom app on mobile communication device 200 to confirm that machine 90 should begin its automated self-test routine.

In step 5, the patient's mobile communication device 200 sends a message to middleware software application at system hub 120 confirming that it is desired for the patient's machine 90 to begin its automated self-test routine. In step 6, middleware software application at system hub 120 sends (e.g., converts and sends) a message to machine 90 indicating that patient 12 has confirmed that machine 90 is to begin its automated self-test routine. In step 7, machine 90 begins and performs its automated self-test routine.

Once the self-test is performed, it is contemplated for system 110c to perform the same steps 1 to seven discussed above, except that the action is now a disinfection procedure instead of the automated self-test routine. Here, the custom app downloaded to the patient's mobile communication device 200 may display a countdown timer to patient 12 reminding the patient how much time the patient has to return to machine 90 to begin treatment. It should be appreciated that different types of medical fluid delivery machines may have different one, two, three or more actions that patient 12 or clinician 112 may perform before treatment begins.

Regarding systems 110a to 110c, it is contemplated to program the app on mobile communication device 200 to be configurable by the user to select which type of notification that the user would like to receive on their device 200, e.g., via the app itself, via text message, and/or via calendar notification. System hub 120 may in one embodiment send all notification types, where mobile communication device 200 ignores the communication types that the user has disabled. System hub 120 in another embodiment stores the user's preferences and only sends information in selected notification types.

Figure 7:
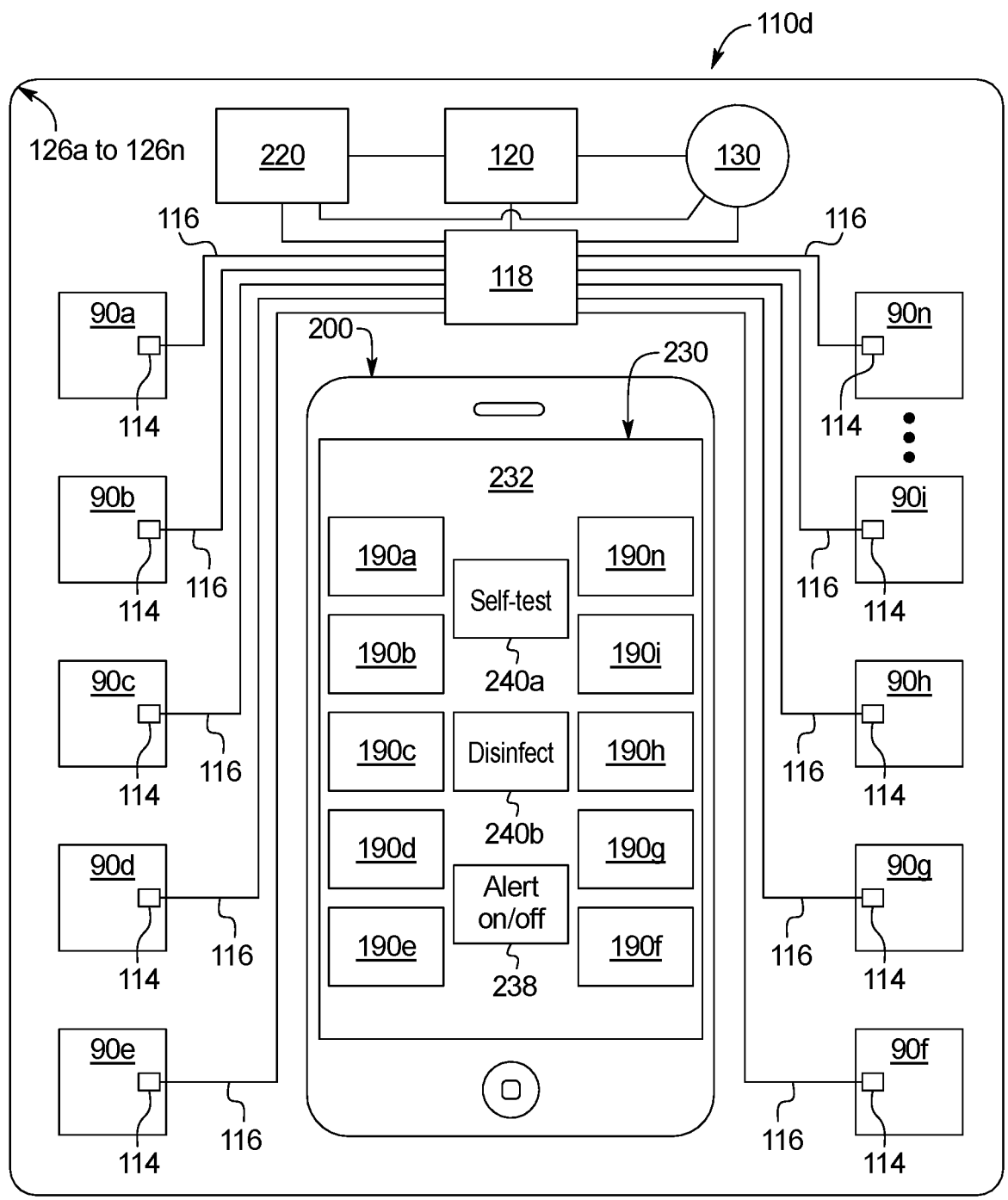
FIG. 7 is a schematic view of one embodiment of a hospital or clinical version of a medical fluid delivery device and data transfer system and method of the present disclosure having a mobile communication device application in a first state.
Figure 8:
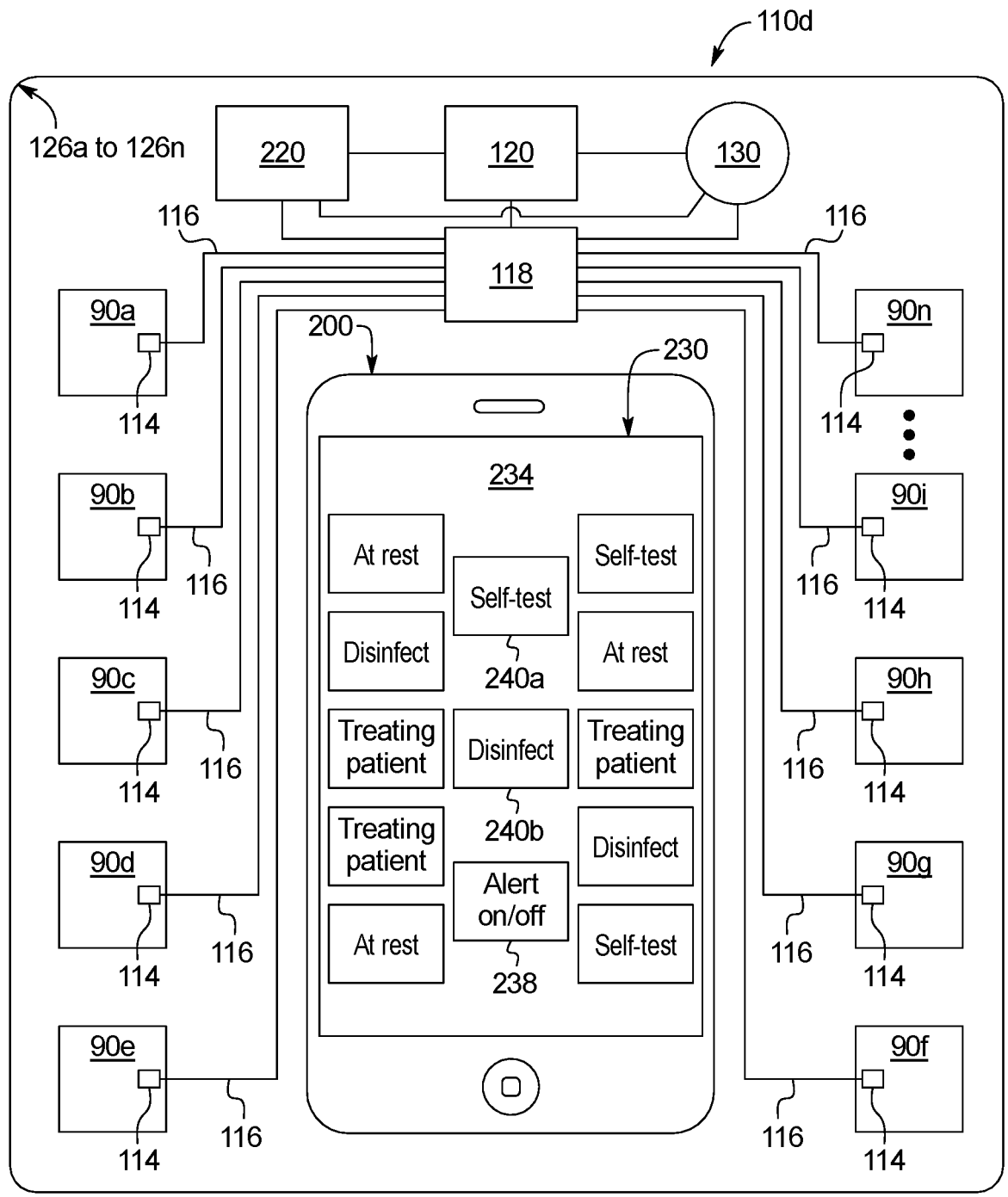
FIG. 8 is a schematic view of one embodiment of a hospital or clinical version of a medical fluid delivery device and data transfer system and method of the present disclosure having a mobile communication device application in a second state.
Figure 9:
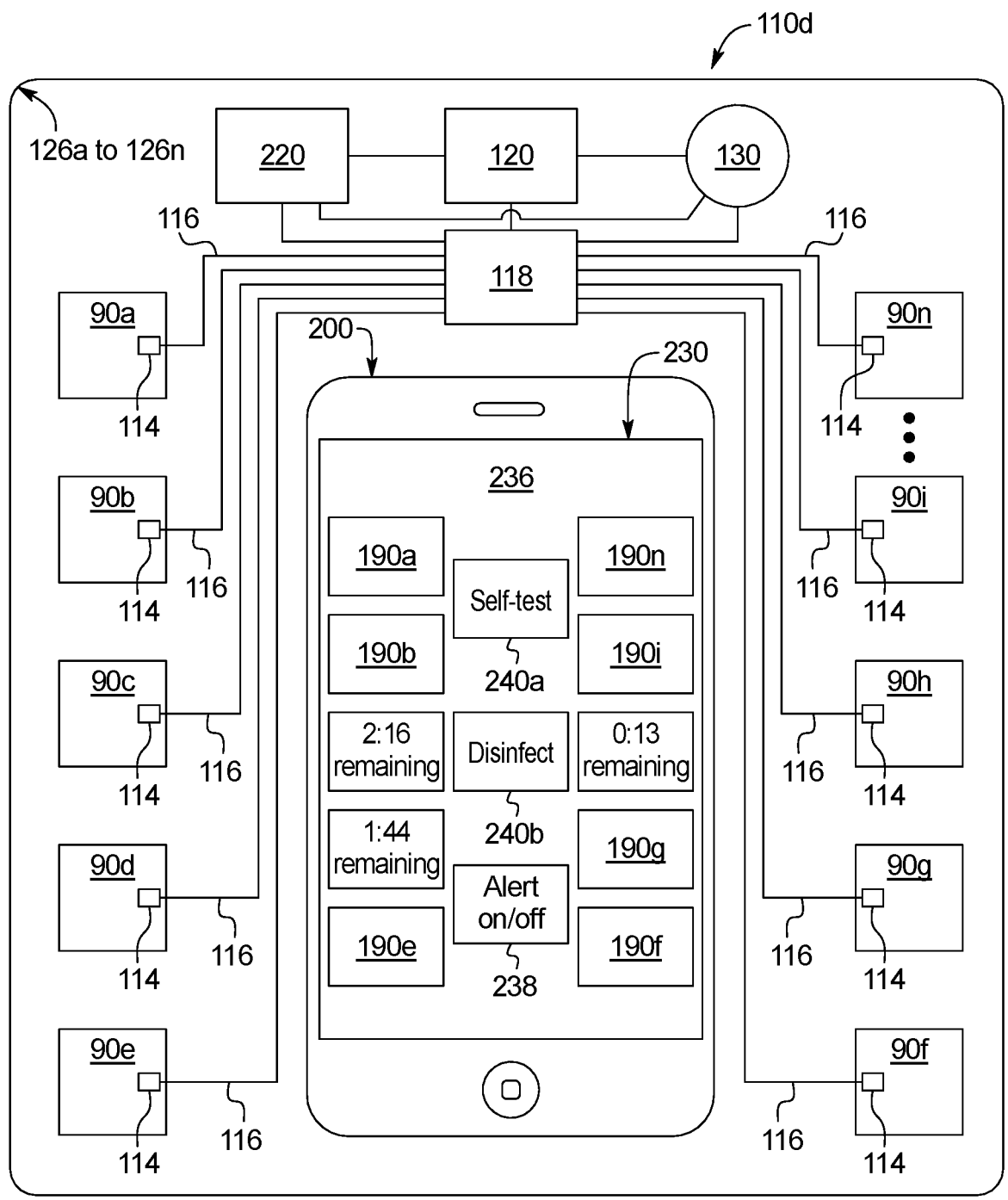
FIG. 9 is a schematic view of one embodiment of a hospital or clinical version of a medical fluid delivery device and data transfer system and method of the present disclosure having a mobile communication device application in a third state.

Referring now to FIGS. 7 to 9, one embodiment of a system 110d having a clinician-based downloadable software application ("app") 230 for a doctor's, clinician's or nurse's mobile communication device 200 is illustrated on screens 232 to 236. As discussed above, mobile communication device 200 may be that of a patient 12 or that of a doctor/nurse/clinician 112. Screens 232 to 236 of FIGS. 7 to 9 illustrate that app 230 may be used in a clinic or hospital 126a to 126n, where a nurse, for example, is responsible for multiple machines 90a to 90n. Machines 90a to 90n may again be hemodialysis machines, peritoneal dialysis machines, CRRT machines, drug and/or nutritional fluid delivery machines and combinations thereof.

Screen 232 illustrates that app 230 may monitor and, if desired, control multiple machines 90. In the illustrated embodiment, machines 90a to 90n are each represented by a dedicated icon 190a to 190n displayed on screen 232 of app 230. Icons 190a to 190n in the illustrated embodiment are ordered the same on screens 232 to 236 as machines 90a to 90n are ordered in clinic 126a to 126c to help orient doctor/nurse/clinician 112.

It is contemplated that app 230 operate with system hub 120 as has been discussed herein, where system hub 120 is remote from clinic or hospital 126a to 126n and is maintained for example by a manufacturer of one or more of machines 90a to 90n. App 230 may for example be developed initially at product development 128 illustrated in FIG. 1. App 230 may then be sent from product development 128 to system hub 120 via service portal 130 as illustrated in FIGS. 1 and 7. Any nurse, clinician or doctor 112 authorized to download app 230 may do so from system hub 120. Thereafter, system hub 120 maintains middleware software to operate with app 230 in the manners described above in systems 110a to 110c.

In an alternative embodiment, clinics 126a to 126n may maintain their own local area networks, each operating with a local system hub 220. App 230 may again be developed by product development 128 (FIG. 1) and delivered via service portal 130 to a local system hub 220 of a clinic 126a to 126n operating with overall system 10. Each nurse, clinician or doctor 112 authorized to download app 230 does so from local system hub 220. Thereafter, local system hub 220 maintains middleware software to operate with app 230 in the manners described above for system hub 120 in systems 110a to 110c. In a further alternative embodiment, app 230 may be developed by clinic 126a to 126n and stored on its local system hub 220.

Middleware software of system hub 120 or local system hub 220 updates the status of each machine 90a to 90n. Nurse, clinician or doctor 112 may select an icon 190a to 190n at any time to see the current status of each machine 90a to 90n, e.g., "at rest", "self-test, "disinfect", or "treating patient" as illustrated in screen 234 of FIG. 8. Other status markers are contemplated and may be different for different types of machines. Nurse, clinician or doctor 112 may then select any of "at rest", "self-test, "disinfect", or "treating patient" to return to the home icons 190a to 190n as illustrated in FIG. 9.

As discussed above, it is contemplated to turn connectivity agent 114 of each machine 90 off when the machine is running and in particular when a patient 12 is connected to the machine. It is also contemplated however to allow connectivity agent 114 of each machine 90a to 90n of clinics 126a to 126n to remain on until the end of disinfection, so that middleware software at system hub 120 or local system hub 220 may receive from each machine 90a to 90n a status change to "treating patient". In addition, because each machine 90a to 90n knows its scheduled treatment duration, the machines may also send to middleware software the scheduled duration, which then sends the duration in the form of a countdown timer along with the status change for "treating patient". Here then, when nurse, clinician or doctor 112 selects "treating patient" in FIG. 8, they are able to see a countdown timer showing the time of treatment remaining as illustrated in FIG. 9.

It is contemplated that for the countdown timers, connectivity agent 114 allows machines 90a to 90n to send time remaining data to system hub 120, so that app 230 may display the actual time remaining for each machine 90 undergoing a timed process. App 230 takes into account alarms or other delays that machines 90 may experience. During an alarm situation, the corresponding icon 190a to 190f may display a message such as "alarm" or "safe mode". Nurse, clinician or doctor 112 may then select the countdown time in FIG. 9 to return to the home icons 190c, 190d, and 190h illustrated in FIG. 7.

Nurse, clinician or doctor 112 may also toggle an alert on/off icon 238 to either allow or not allow status changes for machines 90a to 90n to be alerted visually, audibly and/or haptically. If alert on/off icon 238 is switched to "on", app 230 of mobile communication device 200 will provide a visual, audible and/or haptic alert each time a machine's status changes, e.g., (i) self-test started, (ii) self-test completed, (iii) disinfection started, (iv) disinfection completed, (v) treatment started, (vi) treatment completed. In an embodiment, codes for (i) to (v) are sent via machines 90a to 90n though secure managed connection 116, connectivity server 118 and system hub 120 or local system hub 220 to be translated by middleware software and forwarded to app 230, which updates the appropriate icon 190. In various embodiments, "(vi) treatment completed" may be (a) sent via machines 90a to 90n with connectivity agent 114 activated or (b) inferred when the countdown timer of the appropriate icon 190a to 190n expires, and where connectivity agent 114 may still be off.

If alert on/off icon 238 is switched to off, e.g., if nurse, clinician or doctor 112 does not want to be interrupted at a given moment, icons 190a to 190n are still updated as described above but audible and/or haptic alerts are not provided. Nurse, clinician or doctor 112 may still actively view the status of each machine 90a to 90n, however, by selecting the associated icon 190a to 190n.

Screens 232 to 236 illustrate action buttons 240a and 240b (referred to herein collectively to action buttons 240 or generally individually as action button 240). Any number of action buttons 240 may be provided for any type of pre-treatment action needed for any modality, e.g., hemodialysis, peritoneal dialysis, CRRT, drug and/or nutritional fluid delivery. In the illustrated embodiment, action buttons 240a is for starting a self-test for machines 90, while action button 240b is for starting a disinfection sequence for machines 90.

In one embodiment, when self-test button 240a is selected, any machine 90a to 90n capable at that time of performing a self-test has its corresponding icon 190a to 190n highlighted. Nurse, clinician or doctor 112 selects whichever icon(s) 190 for the machine(s) 90 that the nurse, clinician or doctor 112 wishes to perform a self-test. That selected icon(s) 190 may then turn into a "confirm" button, which the nurse, clinician or doctor 112 has to press again to cause the selected machine(s) 90 to perform its self-test. App 230 of mobile communication device 200 then sends a corresponding self-test code to middleware software at system hub 120 or local system hub 220, which converts, if needed, the self-test code into a self-test initiation command, which is sent via connectivity server 118 over secure managed connection 116 to the connectivity agent 114 of the selected machine 90, which transfers the command to the machine's ACPU 50, which in turn initiates the self-test.

In the illustrated embodiment, when disinfection button 240*b* is selected, any machine 90*a* to 90*n* capable at that time of performing disinfection has its corresponding icon 190*a* to 190*n* highlighted. Nurse, clinician or doctor 112 selects whichever icon(s) 190 for the machine(s) 90 that the nurse, clinician or doctor 112 wishes to perform disinfection. That selected icon(s) 190 may again turn into a "confirm" button, which the nurse, clinician or doctor 112 has to press again to cause the selected machine(s) 90 to perform its disinfection. App 230 of mobile communication device 200 then sends a corresponding disinfection code to middleware software at system hub 120 or local system hub 220, which converts, if needed, the disinfection code into a disinfection initiation command, which is sent via connectivity server 118 over secure managed connection 116 to the connectivity agent 114 of the selected machine 90, which transfers the command to the machine's ACPU 50, which in turn initiates disinfection.

The procedure just described for action buttons 240 may also be implemented in system 110*c* and be implemented for other machine commands, which may vary depending on the type of machine 90. It is also contemplated that a clinic 126*a* may decide that it is safe enough with one or more nurse, clinician or doctor 112 present at the clinic to leave connectivity agent 114 on during treatment or a portion of treatment. In such case, nurse, clinician or doctor 112 may control in-treatment activities for machines 90. For example, nurse, clinician or doctor 112 may receive and respond to alarms/alerts via app 230 at mobile connection device 200, start and stop pumps and other facets of treatment, start and stop disinfection, start and stop priming, and the like.

Each of systems 110*a* to 110*d* operates with some form of addressing. As discussed above, connectivity server 118 is provided in one embodiment to ensure that data is delivered in the proper form to the proper machine 90, and that data from a machine 90 is delivered in its proper form to the proper destination. In one embodiment, when a machine 90 sends data to system hub 120 or local system hub 220 for delivery to a mobile communication device 200, the data is provided with a machine identifier that identifies the machine 90 from which the data was sent. Connectivity server 118 knows each mobile communication device 200 to which a particular machine's data belongs and tells system hub 120 or local system hub 220 which communication devices 200 are to receive the data. System hub 120 or local system hub 220 may then convert the data as has been discussed herein. When sending the, e.g., converted, data, system hub 120 or local system hub 220 may strip the machine identifier from the data since it is not needed anymore. In system 110*d*, however, the machine identifier may be delivered along with the, e.g., converted, data so that app 230 knows which icon 190*a* to 190*n* to populate with the new data. Here, app 230 may strip the machine identifier once it is not needed anymore.

In one embodiment, when a mobile communication device 200 sends data to system hub 120 or local system hub 220 for delivery to a machine 90, the data is provided with a mobile communication device 200 identifier that identifies the mobile communication device 200 from which the data was sent. System hub 120 or local system hub 220 may or may not convert the data from mobile communication device 200 as discussed above, but in either case, the mobile communication device 200 identifier is maintained for connectivity server 118. Connectivity server 118 knows which machine 90 is to receive the, e.g., converted, data for each mobile communication device 200, and sends the, e.g., converted, data to each associated communication device 200. Connectivity server 118 may strip the mobile communication device 200 identifier from the data once delivered to machine 90 since it is no longer needed.

App 230 as described above allows nurse, clinician or doctor 112 to setup, monitor and perhaps control treatment at a medical fluid delivery machine 90. It is contemplated to provide similar functionality via an app to patient 12 or a caregiver for patient 12 at the patient's home (dashed box in FIG. 1). Connectivity may be the same as shown in FIGS. 7 to 9. However, the setting is not a clinic 126*a* to 126*n*, but is instead the home or other non-clinical location such as a business or vacation location. In addition, there is typically only a single machine 90, not multiple machines 90*a* to 90*n*. It is possible however that a single patient 12 may be treated via multiple machines 90, which could each be supported by the app as described herein. If patient 12 is at home but away from machine 90, the app may provide valuable information, such as amount of time left for starting or completing a start-up procedure task, a disinfection procedure or a self-test routine. When the patient is being treated by machine 90, he/she can see information on its user interface 122, which may itself be a tablet as illustrated in FIG. 1. But there may also be a caregiver that helps patient 12 at home during treatment, such as a spouse, friend, or in-home nurse. The caregiver benefits from the home app by receiving status updates, start-up procedure time remaining, disinfection time remaining, priming time remaining, treatment time remaining, information regarding whether or not patient 12 is connected to machine 90, alerts, alarms, and the like. The app in one embodiment requires a login and password associated with the patient to be entered before it can be downloaded to the caregiver's mobile communication device 200, so that only authorized people can view patient treatment data.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical fluid delivery system comprising:
a first medical fluid delivery machine including a first processor and first memory, the first memory storing first instructions, which when executed by the first processor, cause the first processor to
generate, upon completion of a procedure at the first medical fluid delivery machine or upon determining that a preprogrammed time has approached, a first message for remote transmission to a first patient or caregiver indicating (i) that the first medical fluid delivery machine is ready to perform a preprogrammed task or (ii) the preprogrammed time for the first medical fluid delivery machine to perform the same or a different preprogrammed task, and
after receiving a confirmation message from the first patient or caregiver, perform the preprogrammed task or perform at the preprogrammed time the same or the different preprogrammed task; and
a second medical fluid delivery machine including a second processor and second memory, the second memory storing second instructions, which when executed by the second processor, cause the second processor to generate, upon completion of a procedure at the second medical fluid delivery machine or upon determining that a preprogrammed time has approached, a second message for remote transmission to a second patient or caregiver indicating (i) that the second medical fluid delivery machine is ready to perform the same or a different preprogrammed task or (ii) the preprogrammed time for the second medical fluid delivery machine to perform the same or the different preprogrammed task, and after receiving a confirmation message from the second patient or caregiver, perform the same or the different preprogrammed task or perform at the preprogrammed time the same or the different preprogrammed task, wherein the same or the different preprogrammed task includes at least one of preparing medical fluid for a dialysis treatment or pumping a fluid through the respective medical fluid delivery machine, and wherein the same or the different preprogrammed task is configured to be performed (a) before a dialysis treatment is performed on the respective first or second patient, and (b) regardless of whether the respective first or second patient is present at the respective first or second medical fluid delivery machine.

2. The medical fluid delivery system of claim 1, wherein the first and second medical fluid delivery machines are in data communication with at least one server, the first and second messages delivered to the server, the server configured to (i) relay the first message to a first mobile communication device for the first patient or caregiver and (ii) relay the second message to a second mobile communication device for the second patient or caregiver.

3. The medical fluid delivery system of claim 2, wherein the at least one server includes at least one dedicated server or a cloud server.

4. The medical fluid delivery system of claim 2, wherein relaying at least one of the first or second messages includes using a cellular network networking the at least one server and at least one of the first or second mobile communication devices.

5. The medical fluid delivery system of claim 4, wherein communication over the cellular network is via a Short Messaging Service ("SMS") or Multimedia Messaging Service ("MMS") protocol.

6. The medical fluid delivery system of claim 2, wherein the first and second medical fluid delivery machines are home machines in data communication with the at least one server via an internet connection.

7. The medical fluid delivery system of claim 2, wherein the first and second medical fluid delivery machines are in-center machines, wherein the at least one server is maintained at the center.

8. The medical fluid delivery system of claim 2, wherein relaying by the at least one server of at least one of the first or second messages includes updating a software application downloaded onto at least one of the first or second mobile communication devices.

9. The medical fluid delivery system of claim 8, wherein the at least one software application is downloaded from the system.

10. The medical fluid delivery system of claim 2, wherein relaying by the at least one server of at least one of the first or second messages includes updating a calendar installed on at least one of the first or second mobile communication devices.

11. The medical fluid delivery system of claim 1, wherein a start-up procedure task is preprogrammed so as to be performed when at least one of the first patient is away from the first medical fluid delivery machine or the second patient is away from the second medical fluid delivery machine.

12. The medical fluid delivery system of claim 1, wherein a disinfection procedure task or a self-test routine task is preprogrammed so as to be performed when at least one of the first patient is away from the first medical fluid delivery machine or the second patient is away from the second medical fluid delivery machine.

13. The medical fluid delivery system of claim 1, wherein the preprogrammed time for at least one of the first or second medical fluid delivery machines is (i) a set duration from when the first or second message is generated or (ii) a time programmed for the same or a different preprogrammed task to begin.

14. A medical fluid delivery system comprising:
a medical fluid delivery machine including a processor and memory, the memory storing instructions, which when executed by the processor, cause the processor to
generate, upon completion of a procedure at the medical fluid delivery machine or upon determining that a preprogrammed time has approached, a message indicating (i) that the medical fluid delivery machine is ready to perform a preprogrammed task or (ii) a preprogrammed time for the medical fluid delivery machine to perform the same or a different preprogrammed task, and
after receiving a confirmation message in response to the message, perform the preprogrammed task or perform at the preprogrammed time the same or the different preprogrammed task; and
at least one server in data communication with the medical fluid delivery machine to receive the message, the at least one server including middleware software for relaying the message from the medical fluid delivery machine to a remote mobile communication device,
wherein the remote mobile communication device transmits the confirmation message to the server after receiving the message, and the middleware software of the server transmits the confirmation message to the medical fluid delivery machine,
wherein the same or the different preprogrammed task includes at least one of preparing medical fluid for a dialysis treatment or pumping a fluid through the medical fluid delivery machine, and
wherein the same or the different preprogrammed task is configured to be performed (a) before a dialysis treatment is performed on a patient, and (b) regardless of whether the patient is present at the medical fluid delivery machine.

15. The medical fluid delivery system of claim 14, wherein the middleware software updates a software application downloaded onto the mobile communication device to relay the message.

16. The medical fluid delivery system of claim 14, wherein the middleware software updates a calendar installed on the mobile communication device to relay the message.

17. The medical fluid delivery system of claim 14, wherein the middleware software uses a cellular communications network networking the at least one server and the remote mobile communication device to relay the message.

18. The medical fluid delivery system of claim 14, wherein the at least one server includes at least one dedicated server or a cloud server.

19. A medical fluid delivery system comprising:
a medical fluid delivery machine including a processor and memory, the memory storing instructions, which when executed by the processor, cause the processor to generate, upon completion of a procedure at the medical fluid delivery machine, a message indicating that the medical fluid delivery machine is ready to perform a preprogrammed task, and
after receiving a notification in response to the message, perform the preprogrammed task; and
at least one server in data communication with the medical fluid delivery machine via a first link to receive the message, the at least one server configured to (i) relay the message from the medical fluid delivery machine to a remote mobile communication device via a second link, (ii) receive a response from the remote mobile communication device indicating to start the preprogrammed task via the second link, and (iii) send the notification to the medical fluid delivery machine to start the preprogrammed task via the first link,
wherein the preprogrammed task includes at least one of preparing medical fluid for a dialysis treatment or pumping a fluid through the medical fluid delivery machine, and
wherein the preprogrammed task is configured to be performed (a) before a dialysis treatment is performed on a patient, and (b) regardless of whether the patient is present at the medical fluid delivery machine.

20. The medical fluid delivery system of claim 19, wherein the first link is an internet link.

21. The medical fluid delivery system of claim 19, wherein the second link is an internet link or a cellular communications network link.

22. The medical fluid delivery system of claim 19, wherein the at least one server includes at least one dedicated server or a cloud server.

23. A mobile communication device comprising:
a first link to a first medical fluid delivery machine, the first link enabling the mobile communication device to receive a first message from the first medical fluid delivery machine after the first medical fluid delivery machine has at least one of completed a procedure or determined that a preprogrammed time has approached, the first message indicating (i) that the first medical fluid delivery machine is ready to perform a preprogrammed task or (ii) the preprogrammed time for the first medical fluid delivery machine to perform the same or a different preprogrammed task; and
a second link to a second medical fluid delivery machine, the second link enabling the mobile communication device to receive a second message from the second medical fluid delivery machine after the second medical fluid delivery machine has at least one of completed a procedure or determined that a preprogrammed time has approached, the second message indicating (i) that the second medical fluid delivery machine is ready to perform the same or a different preprogrammed task or (ii) the preprogrammed time for the second medical fluid delivery machine to perform the same or a different preprogrammed task,
wherein the mobile communication device transmits a confirmation message to the respective medical fluid delivery machine after receiving the respective message, the confirmation message causing the respective medical fluid delivery machine to perform the preprogrammed task or perform at the preprogrammed time the same or the different preprogrammed task,
wherein the same or the different preprogrammed task includes at least one of preparing medical fluid for a dialysis treatment or pumping a fluid through the respective medical fluid delivery machine, and
wherein the same or the different preprogrammed task is configured to be performed (a) before a dialysis treatment is performed on a patient, and (b) regardless of whether the patient is present at the respective medical fluid delivery machine.

24. The mobile communication device of claim 23, wherein the first and second links include first and second icons, respectively, on a screen of the mobile communication device, the first and second icons associated with the first and second medical fluid delivery machines, respectively.

25. The mobile communication device of claim 24, wherein the first and second icons are associated with the first and second messages, respectively.

26. The mobile communication device of claim 24, wherein at least one of the first or second icons is user selectable to view the first or second message, respectively.

27. The mobile communication device of claim 24, wherein the first and second icons are arranged on the mobile communication device according to how the first and second medical fluid delivery machines are arranged at a facility.

28. The mobile communication device of claim 24, which includes at least one action icon that is user selectable to cause at least one of the first or second medical fluid delivery machines to perform the same or the different preprogrammed task.

29. The mobile communication device of claim 28, wherein the at least one action icon is operated in combination with the first or second icons to select at least one of the first or second medical fluid delivery machines, respectively, to perform the same or the different preprogrammed task.

* * * * *